(12) United States Patent
Ozcan et al.

(10) Patent No.: US 10,365,214 B2
(45) Date of Patent: Jul. 30, 2019

(54) METHOD AND DEVICE FOR DETECTION AND SPATIAL MAPPING OF MERCURY CONCENTRATION IN WATER SAMPLES

(71) Applicant: THE REGENTS OF THE UNIVERSITY OF CALIFORNIA, Oakland, CA (US)

(72) Inventors: Aydogan Ozcan, Los Angeles, CA (US); Qingshan Wei, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 163 days.

(21) Appl. No.: 15/111,472

(22) PCT Filed: Jan. 12, 2015

(86) PCT No.: PCT/US2015/011032
§ 371 (c)(1),
(2) Date: Jul. 13, 2016

(87) PCT Pub. No.: WO2015/108820
PCT Pub. Date: Jul. 23, 2015

(65) Prior Publication Data
US 2016/0327473 A1    Nov. 10, 2016

Related U.S. Application Data

(60) Provisional application No. 61/927,440, filed on Jan. 14, 2014.

(51) Int. Cl.
*G01N 21/31* (2006.01)
*H04N 5/232* (2006.01)
(Continued)

(52) U.S. Cl.
CPC ..... *G01N 21/3151* (2013.01); *G01N 33/1813* (2013.01); *G06T 7/0012* (2013.01);
(Continued)

(58) Field of Classification Search
CPC .......... G01N 21/3151; G01N 33/1813; G01N 2201/062; G01N 2201/0638;
(Continued)

(56) References Cited

U.S. PATENT DOCUMENTS 7,666,318 B1 * 2/2010 Lehtinen ................ B01D 15/00
210/660
2004/0117117 A1 * 6/2004 Sohl, III ................... E02D 1/02
702/2

(Continued)

FOREIGN PATENT DOCUMENTS

| JP | WO000221122 A1 * | 6/2001 |
| WO | 90/14627 A1 | 11/1990 |
| WO | WO2011020187 A1 * | 8/2010 |

OTHER PUBLICATIONS

Kaoutit, Hamid El et al., Sub-ppm quantification of Hg(ll) in aqueous media using both the naked eye and digital information from pictures of a colometric sensory polymer membrane taken with the digital camera of a conventional mobile phone, Anal. Methods, 2013, 5, 54-58.

(Continued)

*Primary Examiner* — Zaihan Jiang
(74) *Attorney, Agent, or Firm* — Vista IP Law Group LLP

(57) ABSTRACT

The concentration of mercury in a sample is measured by a reader secured to a camera-containing mobile electronic device. The reader has holders for sample and control solutions. First and second light sources emitting light at different colors illuminate the sample and control holders. Each holder contains gold nanoparticles, thymine-rich (Continued)

aptamers, and sodium chloride. The light sources illuminate the sample and control holders. An image is captured of the transmitted light through the sample and control holders, wherein the image comprises two control regions of interest and two sample regions of interest. The device calculates the intensity of the two control regions of interest and the two sample regions of interest and generates intensity ratios for the sample and control, respectively, at each color. The device calculates a normalized color ratio based on the intensity ratios and outputs a concentration of mercury based on the normalized color ratio.

19 Claims, 15 Drawing Sheets

Specification includes a Sequence Listing.

(51) Int. Cl.
H04N 5/235 (2006.01)
G06T 7/40 (2017.01)
G01N 33/18 (2006.01)
G06T 7/00 (2017.01)
H04N 5/225 (2006.01)
G06T 7/90 (2017.01)
G01N 15/06 (2006.01)

(52) U.S. Cl.
CPC .............. *G06T 7/90* (2017.01); *H04N 5/2251* (2013.01); *H04N 5/23293* (2013.01); *G01N 2015/0693* (2013.01); *G01N 2201/062* (2013.01); *G01N 2201/0638* (2013.01); *G01N 2201/127* (2013.01); *G06T 2207/30148* (2013.01)

(58) Field of Classification Search
CPC . G01N 2201/127; G06T 7/0012; G06T 7/408; G06T 2207/30148; H04N 5/2251; H04N 5/23293
USPC ............................................................ 348/87
See application file for complete search history.

(56) References Cited

U.S. PATENT DOCUMENTS

| | | | | |
|---|---|---|---|---|
| 2011/0092377 | A1* | 4/2011 | Agrawal | G01N 21/643 506/7 |
| 2011/0262364 | A1* | 10/2011 | Wang | A61K 31/315 424/9.6 |
| 2012/0015445 | A1 | 1/2012 | Kellner et al. | |
| 2012/0123686 | A1* | 5/2012 | Xiang | G01N 33/48792 702/19 |
| 2013/0043142 | A1* | 2/2013 | Bar-Or | G01N 33/49 205/782 |
| 2014/0050641 | A1* | 2/2014 | Ergang | B01D 53/64 423/210 |
| 2014/0106461 | A1* | 4/2014 | Gunther | G01N 33/2025 436/81 |
| 2014/0274667 | A1* | 9/2014 | Alptekin | B01J 20/041 502/80 |
| 2015/0308995 | A1* | 10/2015 | Chen | G01N 27/125 422/98 |
| 2016/0033391 | A1* | 2/2016 | Stroganov | G01N 21/3103 356/326 |
| 2016/0123946 | A1* | 5/2016 | Dufresne | G01N 21/3103 356/437 |
| 2016/0187532 | A1* | 6/2016 | Hurley | E21B 49/02 702/12 |

OTHER PUBLICATIONS

Lee, Jae-Seung et al., Chip-Based Scanometric Detection of Mercuric Ion Using DNA-Functionalized Gold Nanoparticels, Anal. Chem. 2008, 80, 66805-6808.
Li, Li et al., Label-free aptamer-based calorimetric detection of mercury ions in aqueous media using unmodified gold nanoparticles as colorimetric prove, Anal Bioanal Chem (2009) 393:2051-2057.
Liu, Dingbin et al., Gold nanoparticles for the colorimetric and fluorescent detection of ions and small organic molecules, Nanoscale, 2011, 3, 1421-1433.
Miyake, Yoko et el., MercuryII-Mediated Formation of Thymine-HgII-Thymine Base Pairs in DNA Duplexes, J. Am. Chem. Soc. 2006, 128, 2172-2173.
Preechaburana, Pakorn et al., Surface Plasmon Resonance Chemical Sensing on Cell Phones, Angew. Chem. Int. Ed. 2012, 51, 11585-11588.
Tanaka, Yoshiyuki et al., 15N-15N J-Coupling Across HgII: Direct Observation of HgII-Mediated T-T Base Pairs in a DNA Duplex, J. Am. Chem. Soc. 2007, 129, 244-245.
PCT International Preliminary Report on Patentability (Chapter I of the Patent Cooperation Treaty) for PCT/US2015/011032, Applicant: The Regents of the University of California, Form PCT/IB/326 and 373, dated Jul. 28, 2016 (7pages).
Cho, Eun Seon et al., Ultrasensitive detection of toxic cations through changes in the tunnelling current across films of striped nanoparticles, Nat. Mater. 2012, 11, 978-985.
Chung, Eunsu et al., Trace analysis of mercy(II) ions using aptamer-modified Au/Ag core-shell nanoparticles and SERS spectroscopy in a microdroplet channel, Lab Chip, 2013, 13, 260-266.
Coskun, Ahmet et al., Albumin testing in urine using a smart-phone, Lab Chip, 2013, 13, 4231-4238.
Coskun, Ahmet et al., A personalized food allergen testing platform on a cellphone, Lab Chip, 2013, 13, 636-640.
Coskun, Ahmet F., et al., Computational imaging, sensing and diagnostics for global health applications, Current Opinion in Biotechnology, 2014, 25:8-16.
Darbha, Gopala et al., Selective Detection of Mercury (II) Ion Using Nonlinear Optical Properties of Gold Nanoparticlels, J. Am. Chem. Soc. 2008, 130, 8038-8043.
Du, Jianjun et al., Colorimetric Detection of Mercury Ions Based on Plasmonic Nanoparticles, Small, 2013, 9, No. 9-10, 1467-1481.
Gallegos, Dustin et al., Label-free biodetection using a smartphone, Lab Chip, 2013, 13, 2124-2132.
Gartia, Mana Ranjan et al., The microelectronic wireless nitrate sensor network for environmental water monitoring, J. Environ. Monit., 2012, 14, 3068-3075.
Huang, Chih-Ching et al., Parameters for selective colorimetric sensing of mercury(II) in aqueous solutions using mecaptopropionic acid-modified gold nanoparticles, Chem. Commun., 2007, 1215-1217.
Kaoutit, Hamid El et al., Sub-ppm quantification of Hg(II) in aqueous media using both the naked eye and digital information from pictures of a colometric sensory polymer membrane taken with the digital camera of a conventional mobile phone, Anal. Methods, 2013, 5, 54-58.
Kim, Youngjin et al., Gold Nanoparticle-Based Sensing of "Spectroscopically Silent" Heavy Metal Ions, . Nano Lett. 2001, 1, 165-167.
Vashist Sandeep Kumar et al., Cellphone-based devices for bioanalytical sciences, Anal Bioanal Chem (2014) 406:3263-3277.
Lafleur, Josiane P. et al., Gold nanoparticle-based optical microfluidic sensors for analysis of environmental pollutants, Lab Chip, 2012, 12, 4651-4656.
Lee, Jae-Seung et al., Chip-Based Scanometric Detection of Mercuric Ion Using DNA-Functionalized Gold Vanoparticels, Anal. Chem. 2008, 80, 66805-6808.

(56) References Cited

OTHER PUBLICATIONS

Lee, Jae-Seung et al., Colorimetric Detection of Mercuric Ion (Hg2+) in Aqueous Media using DNA-Functionalized Gold Nanoparticles, Angew. Chem. 2007, 119, 4171-4174.
Li, Li et al., Label-free aptamer-based colorimetric detection of mercury ions in aqueous media using unmodified gold nanoparticles as colorimetric prove, Anal Bioanal Chem (2009) 393:2051-2057.
Lillehoj, Peter B. et al., Rapid electrochemical detection on a mobile phone, Lab Chip, 2013, 13, 2950-2955.
Lin, Yang-Wei et al., Gold nanoparticle probes for the detection of mercury, lead and copper ions, Analyst, 2011, 136, 863-871.
Liu, Dingbin et al., Gold nanoparticles for the calorimetric and fluorescent detection of ions and small organic molecules, Nanoscale, 2011, 3, 1421-1433.
Liu, Dingbin et al., Highly Robust, Recyclable Displacement Assay for Mercuric Ions in Aqueous Solutions and Living Cells, ACS Nano 2012, 6, 10999-11008.
Miyake, Yoko et el., MercuryII-Mediated Formation of Thymine-HgII-Thymine Base Pairs in DNA Duplexes, J. Am. Chem. Soc. 2006, 128, 2172-2173.
Mudanyali, Onur et al., Integrated rapid-diagnostic-test reader platform on a cellphone, Lab Chip, 2012, 12, 2678-2686.
Navruz, Isa et al., Smart-phone based computational microscopy using multi-frame contact imaging on a fiber-optic array, Lab Chip, 2013, 13, 4015-4023.
O'Driscoll, Stephen et al., A novel camera phone-based platform for quantitative fluorescent sensing, Anal. Methods, 2013, 5, 1904-1908.
Oncescu, Vlad et al., Smartphone based health accessory for colorimetric detection of biomarkers in sweat and saliva, Lab Chip, 2013, 13, 3232-3238.
Preechaburana, Pakorn et al., Surface Plasmon Resonance Chemical Sensing on Cell Phones, Angew. Chem. Int. Ed. 2012, 51, 11585-11588.
Shen, Li et al., Point-of-care colorimetric detection with a smartphone, Lab Chip, 2012, 12, 4240-4243.
Tanaka, Yoshiyuki et al., 15N-15N J-Coupling Across HgII: Direct Observation of HgII-Mediated T-T Base Pairs in a DNA Duplex, J. Am. Chem. Soc. 2007, 129, 244-245.
Tseng, Derek et al., Lensfree microscopy on a cellphone, Lab Chip, 2010, 10, 1787-1792.
Wei, Qingshan et al., Fluorescent Imaging of Single Nanoparticles and Viruses on a Smart Phone, ACS Nano 2013, 7, 9147-9155.
Zhu, Hongying et al., Cost-effective and compact wide-field fluorescent imaging on a cell-phone, Lab Chip, 2011, 11, 315-322.
Zhu, Hongying et al., Cost-effective and rapid blood analysis on a cell-phone, Lab Chip, 2013, 13, 1282-1288.
Zhu, Hongying et al., Optofluidic Fluorescent Imaging Cytometry on a Cell Phone, Anal. Chem. 2011, 83, 6641-6647.
Zhu, Hongying et al., Quantum dot enabled detection of *Escherichia coli* using a cell-phone, Analyst, 2012, 137, 2541-2544.
PCT International Search Report for PCT/US2015/011032, Applicant: The Regents of the University of California, Form PCT/ISA/210 and 220, dated Apr. 29, 2015 (7pages).
PCT Written Opinion of the International Search Authority for PCT/US2015/011032Applicant: The Regents of the University of California, Form PCT/ISA/237, dated Apr. 29, 2015 (5pages).

* cited by examiner

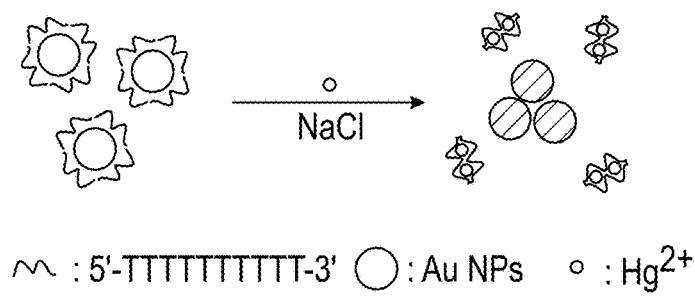
FIG. 2A
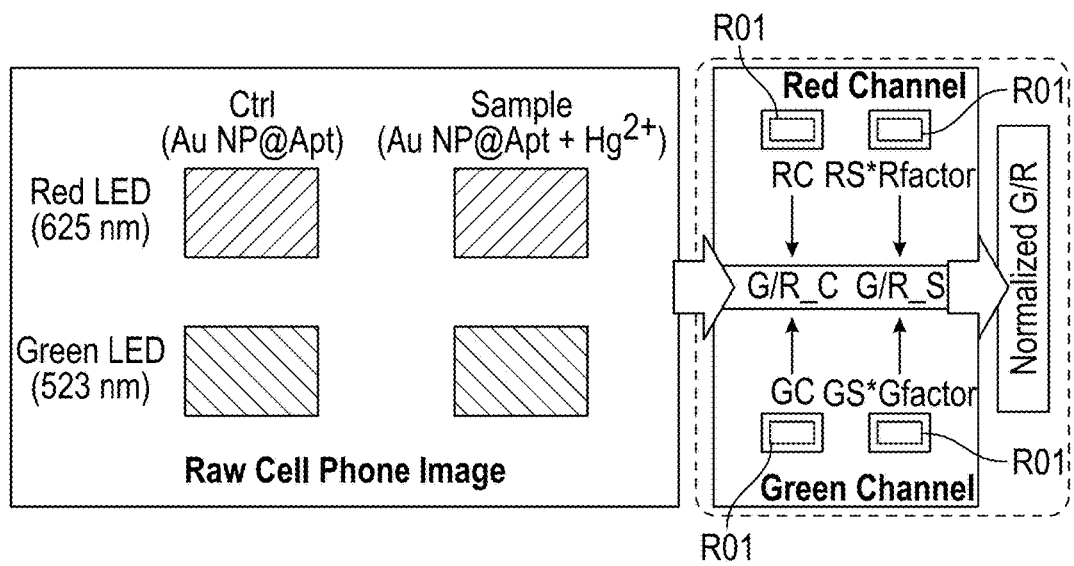
FIG. 2B  FIG. 2C

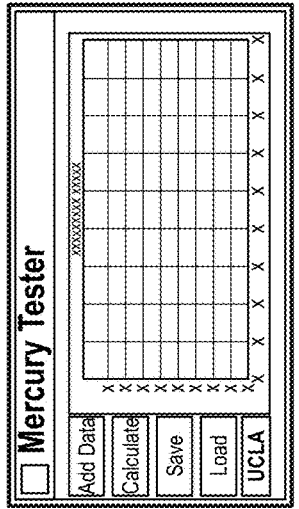
FIG. 4A
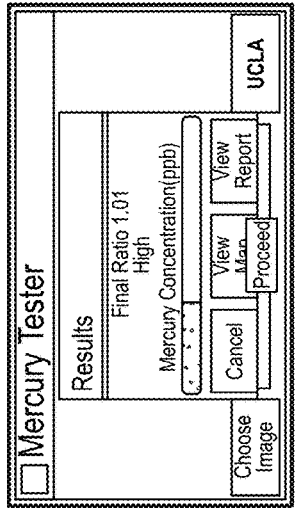
FIG. 4B
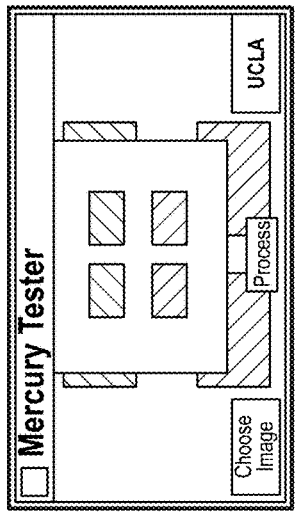
FIG. 4C
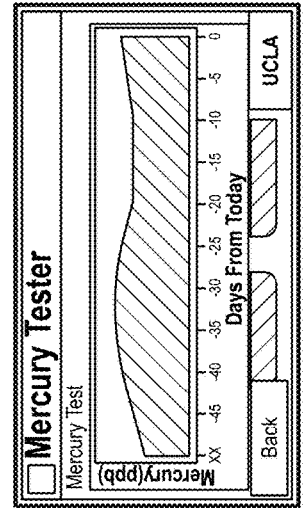
FIG. 4D
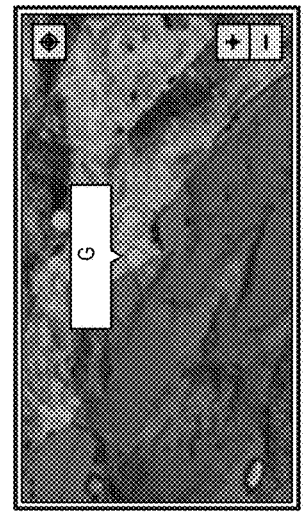
FIG. 4E
FIG. 4F

METHOD AND DEVICE FOR DETECTION AND SPATIAL MAPPING OF MERCURY CONCENTRATION IN WATER SAMPLES

RELATED APPLICATION

This Application is a U.S. National Stage filing under 35 U.S.C. § 371 of PCT Patent Application No. PCT/US2015/011032, filed Jan. 12, 2015, which claims priority to U.S. Provisional Patent Application No. 61/927,440 filed on Jan. 14, 2014. The contents of the aforementioned applications are incorporated by reference herein. Priority is expressly claimed in accordance with 35 U.S.C. §§ 119, 120, 365 and 371 and any other applicable statutes.

STATEMENT REGARDING FEDERALLY SPONSORED RESEARCH AND DEVELOPMENT

This invention was made with government support under Grant Numbers W911NF-11-1-0303 and W911NF-13-1-0197, awarded by the U.S. Army, Army Research Office, and Grant Number OD006427, awarded by the National Institutes of Health and Grant Numbers 0954482 and 1332275, awarded by the National Science Foundation. The government has certain rights in the invention.

FIELD OF THE INVENTION

The technical field generally relates methods and devices for the detection of mercury levels within water. More specifically, the technical field relates to portable devices for the detection and spatial mapping of mercury levels within water. The device, in one embodiment, utilizes a mobile phone device

BACKGROUND

Mercury is a liquid metal found in natural deposits such as ores containing other elements. Mercury is used in dry-cell batteries, fluorescent light bulbs, switches, and other equipment. The major sources of mercury in drinking water are erosion of natural deposits, discharges from refineries and factors, runoff from landfills, and runoff from croplands. Drinking water with high levels of mercury over a long period of time may result in health problems such as kidney damage. The Environmental Protection Agency in the United States has established so-called maximum contaminant levels (MCL) for chemicals such as mercury. MCLs are set as close to the health goals as possible, considering cost, benefits and the ability of public water systems to detect and remove contaminants using suitable treatment technologies. The EPA has set an enforceable regulation for mercury, (MCL), at 0.002 mg/L or 2 ppb. The World Health Organization (WHO) establishes a maximum level of 6 ppb for mercury(II) in drinking water. When routine monitoring indicates that mercury levels are above the MCL, a water supplier must take steps to reduce the amount of mercury so that is below that level. Water suppliers must notify their customers as soon as practical, but no later than 30 days after the system learns of the violation. Additional actions, such as providing alternative drinking water supplies, may be required to prevent serious risks to public health.

Various neurological effects of mercury exposure have been mainly attributed to the organic form of mercury, predominantly methylmercury (MeHg$^+$), which is known to accumulate in the food chain and cross the blood-brain barrier after human ingestion while such findings have added weight to the severity of organic mercury contamination, the threat of inorganic mercury, namely mercury(II) ions (Hg$^{2+}$), should not be underestimated. In fact, mercury (II) ions are the primary mercury contamination in the aquatic system and the "precursor" form of methylmercury due to bacteria-assisted biotransformation processes. Furthermore, inorganic mercury is known to be more nephrotoxic than its organic form as it primarily accumulates in the kidney proximal tubule cells. The detection and quantification of mercury(II) ion contamination in water systems are of paramount importance, and could potentially be used to assist prevention of mercury ions from entering the food chain.

Detection of environmental contamination such as trace-level toxic heavy metal ions mostly rely on bulky and costly analytical instruments. Low nanomolar (nM) concentrations of mercury(II) ions have been traditionally detected by using spectroscopic methods, including e.g., atomic absorption spectroscopy (AAS), inductively coupled plasma-mass spectrometry (ICP-MS), and atomic fluorescence spectrometry (AFS). However, these approaches require complex sample preparation procedures, expensive and bulky instruments, and professionally trained personnel running the tests. Therefore, they are not well suited for rapid on-site detection of mercury and may not even be available for use in developing countries. While relatively inexpensive test strips are available for mercury testing, this requires a user to match the color of the reacted test strip to a set control which may produce inaccurate results. Moreover, such test strip solutions are often not able to detect low or trace levels of heavy metals such as mercury. A considerable global need exists for portable, rapid, specific, sensitive and cost-effective detection techniques that can be used in resource-limited and field settings.

SUMMARY

In one aspect of the invention, a system for analyzing a water sample for mercury with a mobile electronic device having a camera includes a reader configured for securement to the mobile electronic device over the camera. The reader further includes a sample solution holder and a control solution holder. A power source is operatively coupled to a first light source and a second light source via a switch. The first and second light sources are configured to illuminate the sample solution holder and the control solution holder with different colors. A mask is interposed between the first and second light sources and the sample solution and control solution holders, the mask comprising a first set of apertures disposed over the sample solution holder and the control solution holder and configured to be illuminated by the first light source and a second set of apertures disposed over the sample solution holder and the control solution holder and configured to be illuminated by the second light source. A lens is disposed in the reader and positioned adjacent to the camera. A solution containing sodium chloride, nanoparticles, and thymine-rich aptamer contained in both the sample solution holder and the control solution holder, the sample solution holder also containing the water sample therein. The mobile electronic device is configured to capture an image of transmitted light passing through the control solution holder and the sample solution holder from the first and second light sources, wherein the image contains four separate regions of interest and wherein the mobile electronic device outputs a concentration of mercury within the water sample based on a normalized color ratio obtained from a measured intensity levels at each of the four separate regions of interest.

In another embodiment, a method of measuring the concentration of mercury in a water sample includes securing a reader to a mobile electronic device having a camera therein, the reader comprising a sample solution holder and a control solution holder; a power source operatively coupled to first and second light sources configured to illuminate a sample solution holder and a control solution holder at two different colors; and a lens disposed in the reader and adjacent to the camera. The sample solution holder is loaded with the water sample, gold nanoparticles, thymine-rich aptamers, and sodium chloride. The control solution holder is loaded with the gold nanoparticles, thymine-rich aptamers, and, and sodium chloride. The sample solution holder and the control solution holder are illuminated with first and second light sources emitting light. An image of the transmitted light through the sample solution holder and the control solution holder is captured, wherein the image comprises two control regions of interest and two sample regions of interest. The mobile electronic device calculates the intensity of the two control regions of interest and the two sample regions of interest regions of interest and generating intensity ratios for the sample and control, respectively, at each color. The mobile electronic device calculates a normalized color ratio based on the intensity ratios and outputting a concentration of mercury based on the normalized color ratio.

In another embodiment, a method of generating a spatio-temporal contamination map for mercury includes a computer receiving a plurality of measured concentrations of mercury obtained from a plurality of different mobile electronic devices, each mobile electronic device associated with a mercury reading device, wherein the each measured concentration of mercury value is associated with a time stamp and GPS coordinates. The computer populating a map with the plurality of measured mercury concentrations. The computer transfers the populated map to one of the plurality of different mobile devices.

BRIEF DESCRIPTION OF THE DRAWINGS

FIG. 2A illustrates the reaction showing how the presence of mercury causes a thymine-rich aptamer, which normally surrounds gold nanoparticles, to preferentially bind to mercury in the presence of NaCl, thereby leaving exposed nanoparticles that undergo a color change. The color change is used to quantify the concentration of mercury in a sample of water.

FIG. 2B illustrates a raw image obtained of a sample and control using the camera of a mobile communication device that has attached to it the reader mounted thereon for measurement of mercury concentration.

FIG. 2C illustrates the flow of operations used to convert the raw images obtained in FIG. 2B into respective channel images that are used to generate sample and control ratios, and normalized G/R ratio.

FIG. 4A illustrates an illustrative main menu screen that is displayed to a user from an application run on the mobile communication device.

FIG. 4B illustrates an illustrative calibration menu that is displayed to a user from an application run on the mobile communication device.

FIG. 4C illustrates an example of a captured or selected colorimetric image before proceeding to analyzer/quantify the sample.

FIG. 4D illustrates an example of a results screen that is displayed to a user from an application run on the mobile communication device. The mercury concentration in parts per billion is displayed to the user along with the final G/R ratio.

FIG. 4E illustrates spatio-temporal mapping of mercury contamination using a Google Maps-based interface.

FIG. 4F illustrates a graph of mercury concentration results for a single location obtained over multiple time periods.

DETAILED DESCRIPTION OF THE ILLUSTRATED EMBODIMENTS

Figure 1A:
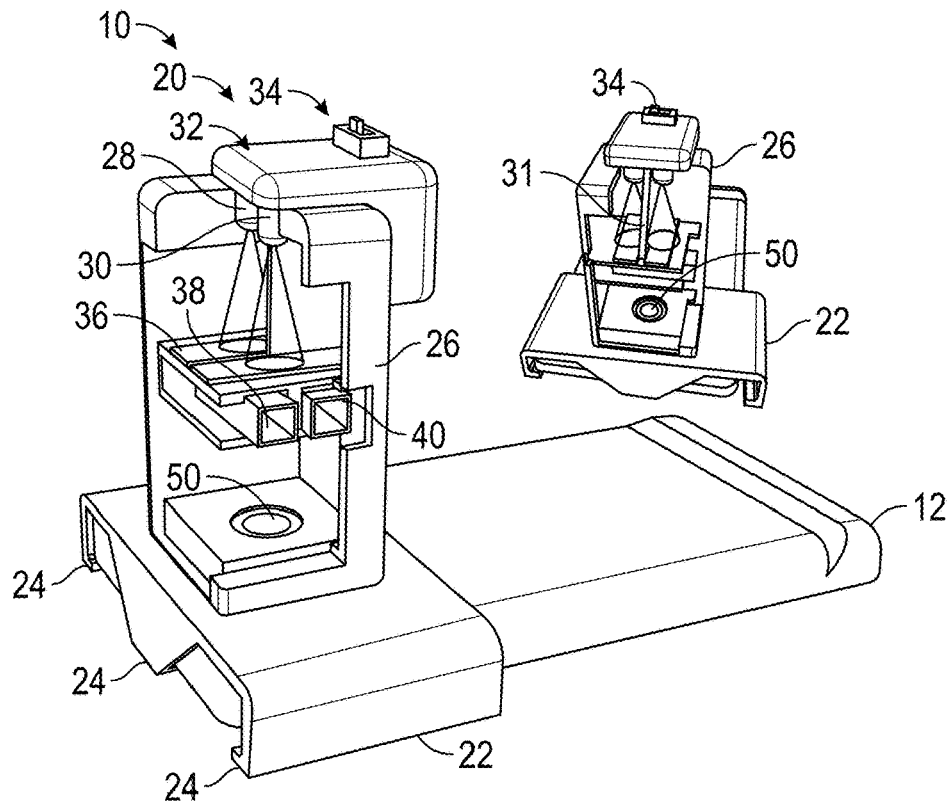
FIG. 1A illustrates a perspective view of a mobile communication device having a reader mounted thereon for testing for mercury concentration.
Figure 1B:
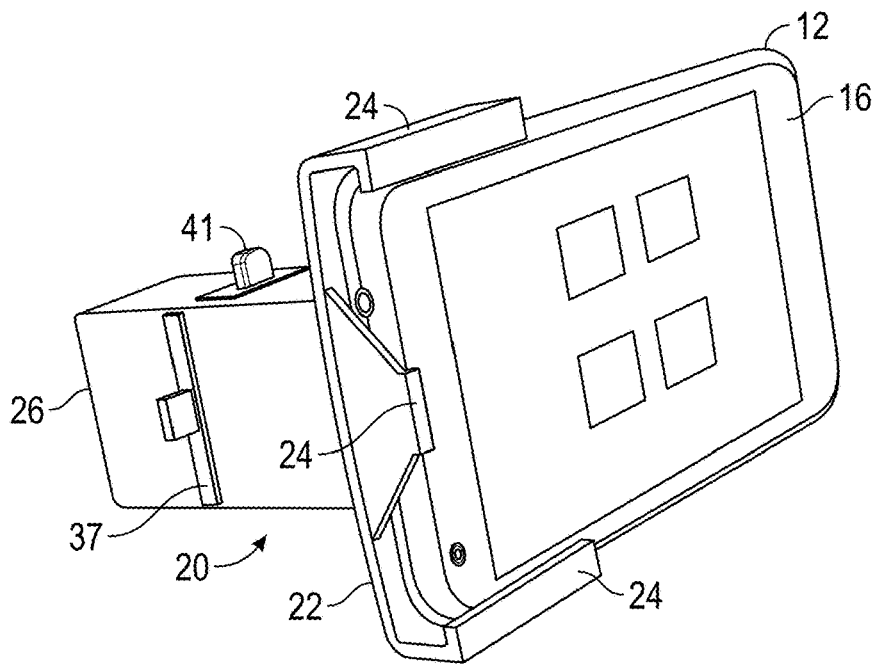
FIG. 1B is another perspective view of the mobile communication device with the reader secured thereto. Four illumination regions (2 sample, 2 control are illustrated) are illustrated on the display of the mobile communication device.
Figure 1C:
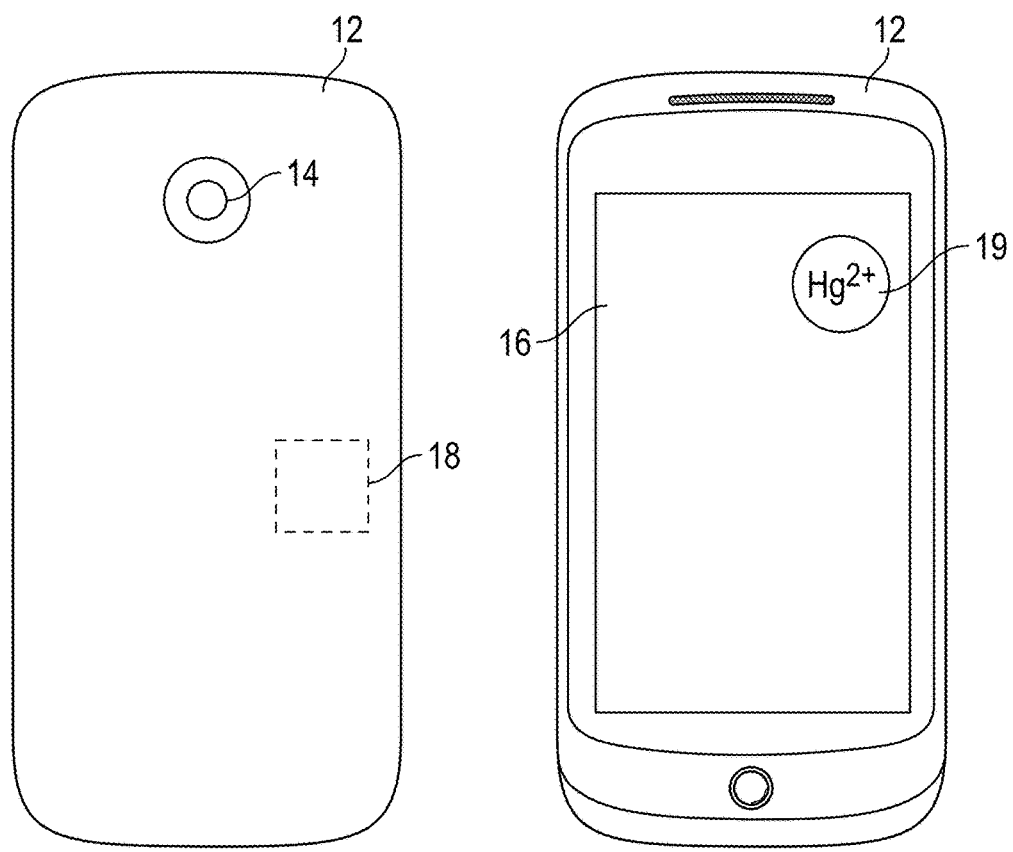
FIG. 1C illustrates front and back views of a mobile phone as the mobile communication device.

FIGS. 1A-1F illustrate a system 10 for analyzing a water sample for mercury according to one embodiment. The system 10 includes a mobile electronic device 12 that is preferably a mobile phone that includes a camera 14 therein. The mobile phone 12 may include a Smartphone or other similar device. Alternatively, the mobile electronic device 12 may include a tablet device that includes a camera 14 therein. As seen in FIG. 1C, the mobile phone 12 includes a camera 14 and a display 16. The mobile phone 12 includes at least one processor 18 therein that is used to operate software or an application on the mobile phone 12 as is known in the art. In one aspect of the invention, the system 10 is accompanied by software or an application "app" 19 that may be downloaded or otherwise stored on the mobile phone 12 and is used in connection with the system 10 to calculate, display, map, and transmit mercury analysis results. The mobile phone 12 typically connects wirelessly with its own proprietary phone network but may also communicate over a WiFi network.

Figure 1D:
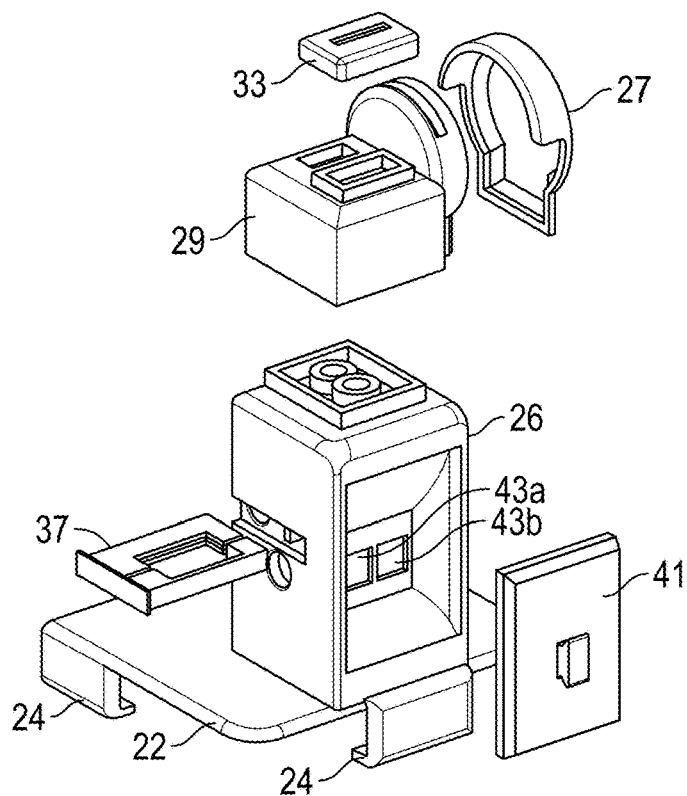
FIG. 1D is an exploded view of another version of a reader that is configured to mount on a mobile communication device. Note that the electrical components such as the batter, switch, two LED light sources are not illustrated in this view.
Figure 1E:
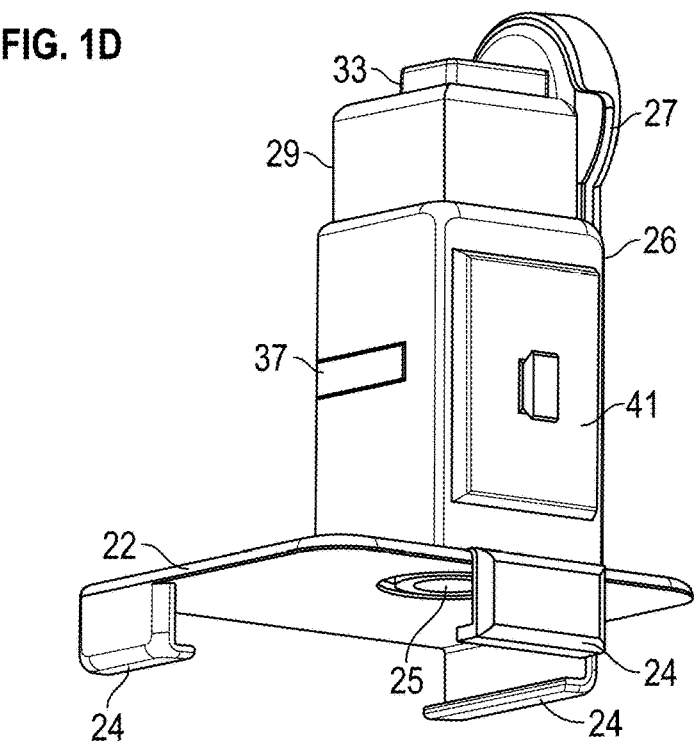
FIG. 1E is a perspective view of the embodiment of FIG. 1D in an assembled state.
Figure 1F:
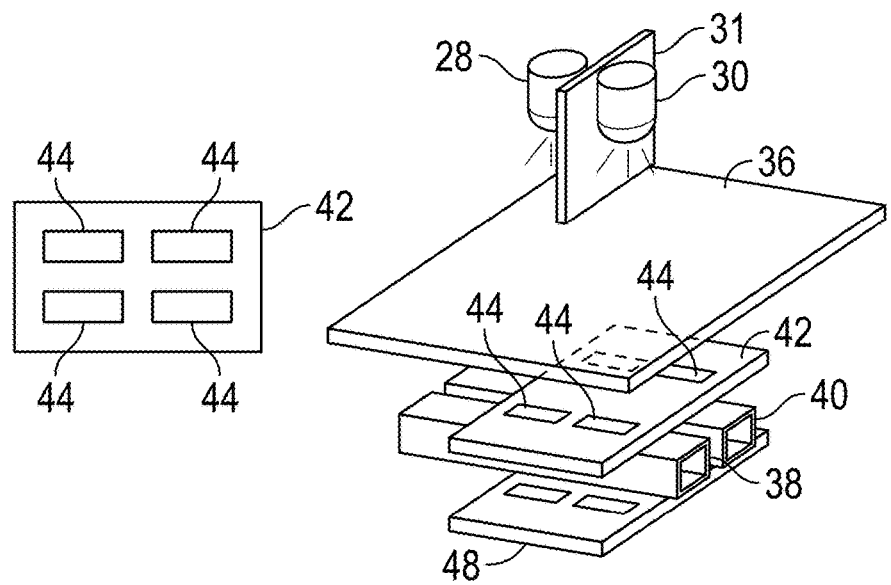
FIG. 1F illustrates the two different colored light sources, the partition, the diffuser, the masks (×2), and the sample solution holder, and the control solution holder.
Figure 1G:
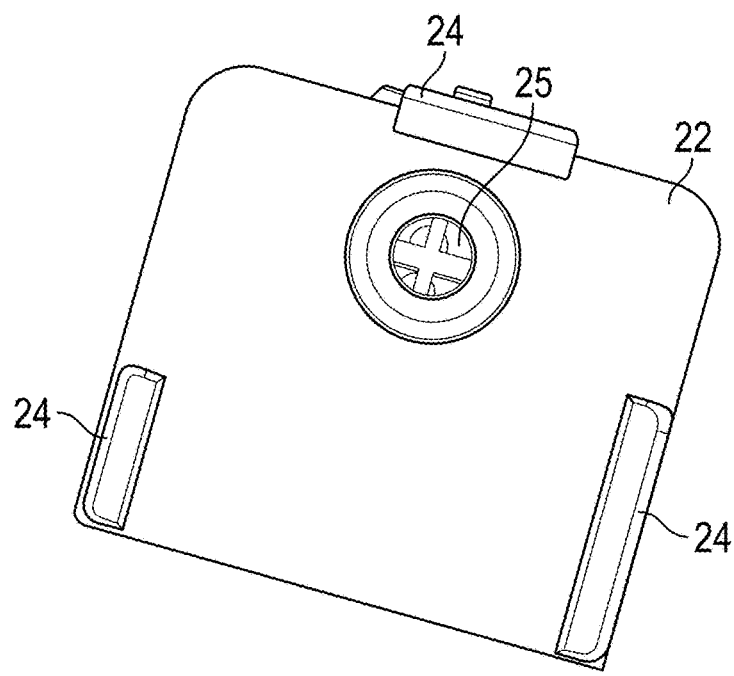
FIG. 1G illustrates the underside of the mounting region of the embodiment illustrated in FIGS. 1D and 1E.

The system 10 includes a reader 20 (FIGS. 1A, 1B, 1D, 1E, and 1G) that is configured to be removeably secured to the mobile phone 12 and includes the components therein that perform a colormetric assay with images being acquired using the camera 14 of the mobile phone 12. The images obtained by the camera 14 are then processed using the application 19 (FIG. 1C) to output a test result that includes the measured concentration of mercury in the tested sample. The reader 20 includes a mounting section 22 (e.g., a face plate) that includes a plurality of clips 24 that dimensioned to secure the reader 20 to a face of the mobile phone 12. The mounting section 22 may be dimensioned to interface with particular sizes or models of different models or makes of mobile phones 12. The mounting section 22 is configured to mount on a face of the mobile phone 12 that contains the camera 14. As seen in FIG. 1E and FIG. 1G the mounting section 22 includes an aperture 25 that provides an optical pathway for transmitted light to reach the camera 14. Typically, the camera 14 is located on the rear or back face of the mobile phone 12 as is illustrated in FIG. 1C.

A housing 26 extends away from the mounting section 22 and is oriented generally orthogonal to the mounting section 22. The housing 26 is situated above the aperture 25 and contains the optical components and sample holder used as part of the testing system 10. The housing 26 includes a first light source 28 and a second light source 30 that are mounted in an upper or top section of the housing 26 are oriented downward to deliver light along an optical pathway that leads through the aperture 25 and into the camera 14. The first and second light sources 28, 30 include, for example, light emitting diodes (LEDs) although other light sources light laser diodes may also be used. The first and second light sources 28, 30 emit light at different colors (i.e., wavelengths). For the mercury test, it is preferable that a first light source 28 emit green colored light (e.g., 523 nm) while the second light source 30 emit red colored light (e.g., 625 nm). The emission wavelengths of the first and second light sources 28, 30 were chosen to follow the shift in the extinction wavelengths of the dispersed and aggregated gold nanoparticles, respectively. It should be understood that other wavelengths could be used. A partition 31 (inset of FIG. 1A and FIG. 1F) may separate the first light source 28 from the second light source 30 to ensure no crosstalk between the first and second light sources 28, 30. A power source 32 is provided in the housing 26 which is used to power the first and second light sources 28, 30. The power source 32 are batteries such as a two 3V button or coin battery. A switch 34 is provided on the housing 26 and is used to selectively turn on/off the first and second light sources 28, 30. Both the first and second light sources 28, 30 are illuminated when the switch 34 is in the "on" state. Likewise, both the first and second light sources 28, 30 are in not illuminated when the switch is in the "off" state.

The housing 26 includes an optical diffuser 36 that is positioned within the optical path of the light emitted from the first and second light sources 28, 30. The optical diffuser 36 ensures uniform illumination of the sample solution holder and control solution holder as explained below. In one aspect of the invention the optical diffuser 36 can be changed. For example, the optical diffuser 36 can be located within a tray 37 (seen in FIG. 1D) that can be pushed into or pulled out of the housing 26 whereby different optical diffusers 36 can be loaded into the tray. Referring to FIGS. 1A and 1F, a sample solution holder 38 and a control solution holder 40 are contained within the housing 26 and located within the optical path formed between the first and second light sources 28, 30 and the camera 14. The sample solution holder 38 and the control solution holder 40 are located some distance from the first and second light sources 28, 30 (e.g., about 26.5 mm). The sample solution holder 38 and a control solution holder 40 may each be formed from an optically transparent material such as glass or plastic. For example, separate rectangular cuvettes may be used for the sample solution holder 38 and a control solution holder 40. A cover 41 as seen in FIGS. 1B and 1D may be placed over sample solution holder 38 and the control solution holder 40 when they are placed inside the housing 26. Interposed between the optical diffuser 36 and the sample solution holder 38 and a control solution holder 40 is a mask 42 as seen in FIG. 1E. The mask 42 includes apertures 44 therein that permit the passage of light to form four (4) separate illumination regions over the sample solution holder 38 and a control solution holder 40. The apertures 44 may be rectangular shaped apertures (e.g., 6.6×5 mm) that are placed directly in front of the sample solution holder 38 and a control solution holder 40. Two apertures 44 form two illumination regions from the first light source 28 on the sample solution holder 38 and control solution holder 40, respectively. The other two apertures 44 form two illumination regions from the second light source 28 on the sample solution holder 38 and control solution holder 40, respectively.

The housing 26 includes another mask 48 disposed on the opposing side of the sample solution holder 38 and control solution holder 40 to collect transmitted light. The mask 48 is the same size and contains the same number (i.e., four) and sized apertures as those in mask 42. The mask 48 ensures the formation of sharply defined and discrete imaging regions on the camera 14. The housing 26 includes a lens 50 that is disposed in the optical path between the sample solution holder 38 and control solution holder 40. The lens 50 may include a plano-convex lens (e.g., f=28 mm). The lens 50 may yield a demagnification factor of 7× so that the sample solution holder 38 and control solution holder 40 can be simultaneously imaged within active area of the images sensor (not shown) of the camera 14. In one embodiment, the housing 26 is relatively small and the total weight of the reader 20 is less than 40 grams.

FIGS. 1D and 1E illustrate an alternative construction of the system 10 that includes a slightly different construction of the housing 26 although the main components and operations of the system 10 are the same as previously described and given the same reference numbers in the drawings. In FIG. 1D, one can see the tray 37 that can be opened/closed to insert the diffuser 36 (not illustrated in FIG. 1D). FIG. 1D also illustrates a larger cover 41 that is used to close isolate the sample solution holder 38 and control solution holder 40 within the interior of the housing 26 that prevents external light from intruding therein. In addition, the battery (not shown) is held on within a circular extension 27 of the housing 26. As seen in FIG. 1D, the housing 26 includes openings 43a, 43b that receive the sample solution holder 38 and control solution holder 40. In the embodiment of FIGS. 1D and 1E, a cap 29 houses the first and second light sources 28, 30 (not shown in FIG. 1D). A switch cover 33 encloses a switch 34 (not shown in FIG. 1D).

The actual mercury test that is used in the system 10 is based on a plasmonic colorimetric assay that uses spherical gold (AU) nanoparticles (NPs). FIG. 2A illustrates the reaction showing how the presence of mercury causes a thymine-rich aptamer, which normally surrounds gold nanoparticles, to preferentially bind to mercury in the presence of NaCl, thereby leaving exposed nanoparticles that undergo a color change. The color change is used to quantify the concentration of mercury in a sample of water.

The characteristic color change of Au NPs from red to purple or blue upon aggregation that is induced by mercury (II) ion binding events constitutes the basis of the Au NP-based colorimetric detection assay. However, most Au NP-based probes require a surface modification step to conjugate mercury(II)-specific ligands onto Au NPs, and the LOD varies based on the capturing ligand that is selected. In the test adopted herein, an alternative approach is taken which utilizes the strong affinity of the thymine-rich aptamer (Apt) sequence to mercury(II) ions and citrate-stabilized Au NPs as colorimetric signal transducers to generate a high detection sensitivity. In this protocol, Au NPs are used without the need for surface functionalization steps, which greatly facilitates field use.

In an exemplary mercury detection experiment, 0.64 nM of Au NPs (50 nm diameter; available from nanoComposix, San Diego, Calif.) are mixed with 3 μM aptamer (5'-TTTTTTTTTT-3') (SEQ ID NO:1) (available from Integrated DNA Technologies) in 20 mM Tris-HCl buffer (pH 8.0) to form the probe solution. Next, 4 μL of water sample solution is added to the probe solution and incubated for 5-10 minutes. Aptamer forms a protective layer on the surface of Au NPs, which prevents them from aggregation even in a high salt environment such as 10 mM NaCl. However, this aptamer layer will be stripped off by the presence of mercury(II) ions due to the formation of more stable T-$Hg^{2+}$-T complexes. As a result, the unprotected Au NPs can undergo distinct color transition from red to blue in the presence of NaCl, and this spectral shift is detected to quantify mercury concentration using the dual-wavelength colorimetric reader system 10 described herein.

To use the system, a water sample is collected from a tested source. The tested source may include an environmental source such as a river, stream, lake, ocean, beach, or even drinking water from a tap. The sample may undergo an optional filtration step using, for example, a polyethersulfone membrane (e.g., 2 μm membrane available from Whatman) to remove sand or other particulates within the sample. Calibration samples that contain mercury(II) ions can be used directly without purification.

In a typical measurement procedure, 4 μL of the sample of interest is injected into a 1.5 mL centrifuge tube and mixed with 4 μL of 3 μM aptamer (20 mM TH buffer, pH 8.0), followed by a 5 minute reaction period. Next, 400 μL of Au NPs (0.64 nM) in 20 mM TH buffer solution was added and allowed to react for 5 minutes. Finally, 8 μL of 10 mM NaCl was added and incubated for another 10 minutes. The sample can then be transferred to the sample solution holder 38 to be analyzed by the system 10 described herein. A control sample is prepared by the same manner with the same components and concentration but without the water sample. Note that in a commercial embodiment, a kit may be provided that includes a container (e.g., vial or tube) that contains the aptamer, Au NPs, buffer, and salt solution already pre-mixed. A sample of water that is obtained can then be added to this solution and placed in the sample solution holder 38. The provided solution can be used as the control solution for the control solution holder 40.

In order to run a test, the reader 20 is secured to the mobile communication device 12 using the clips 24. The reader 20 is positioned such that aperture 25 surrounds the camera 14 of the mobile communication device 12. If not already loaded within the housing 26, the optical diffuser 36 is inserted into the tray 37 and inserted into the housing 26. The sample solution holder 38 and the control solution holder 40 are loaded into the housing 26 by inserting the same into the openings 43a, 43b. After the sample solution holder 38 and the control solution holder 40 have been loaded into the housing 26 and closed via the cover 41, the user can then initiate the software application 19 on the mobile communication device 12. Typically this is done, for example, by selecting the application icon 19 as illustrated in FIG. 1C. The user is then presented with a main menu 100 as illustrated in FIG. 4A. The main menu may provide the user with several options. For example, the user may run a new test, calibrate the device by creating a device-specific calibration curve, share test results, open up a map to see results geographically, or select instructions which provide the user with detailed instructions on how the use the system 10.

Figure 3:
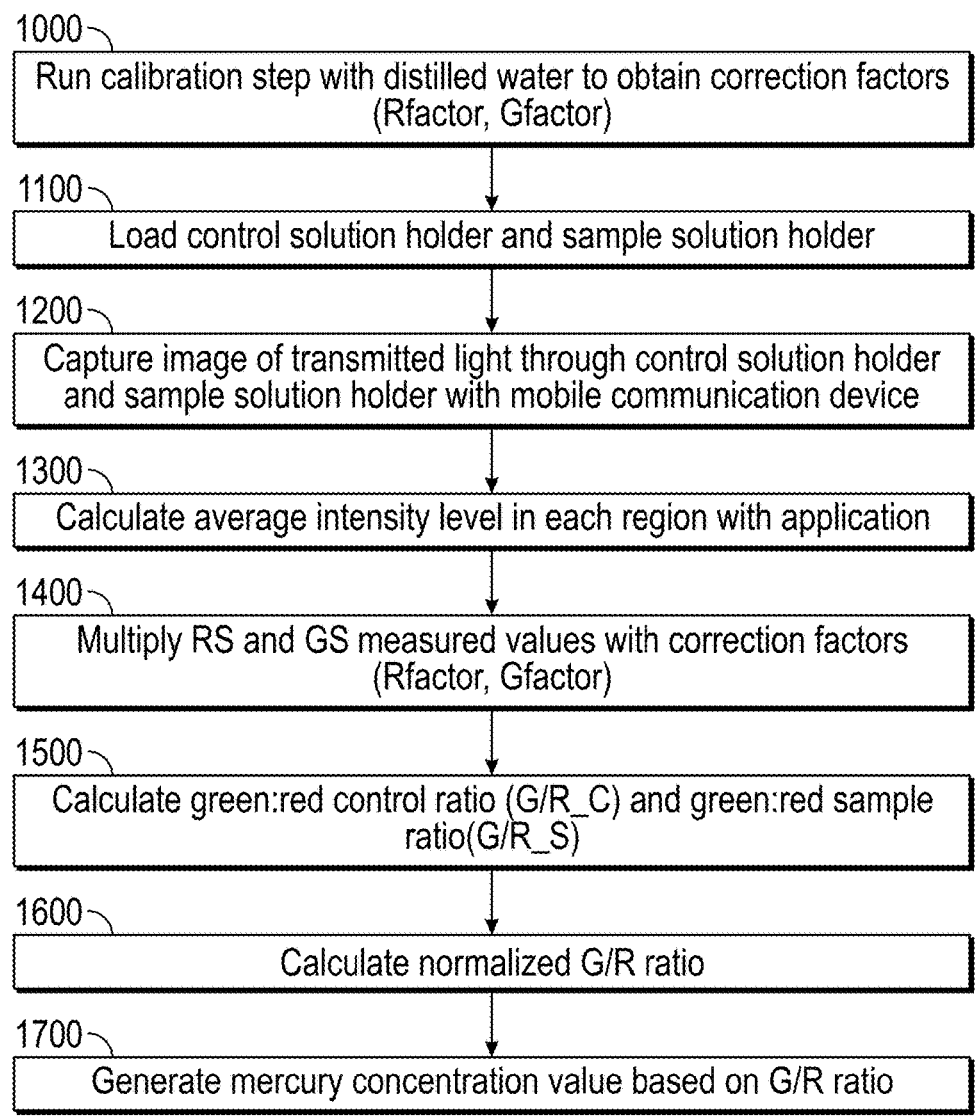
FIG. 3 illustrates a flow chart of the operations used to obtain the concentration of mercury within a sample.

Assuming that user runs a new test, in one embodiment, and with reference to FIG. 3, the first step 1000 is run an initial calibration step with distilled water only contained in both the sample solution holder 38 and the control solution holder 40. This optional operation is performed because there may be slight variations in the illumination received by the sample solution holder 38 and the control solution holder 40. In this operation, the camera 14 obtains an image that contains the four regions of illumination ($Red_{Sample}$, $Red_{Control}$, $Green_{Sample}$, $Green_{Control}$). A region of interest is established within each of the four regions that is slightly smaller than the colored rectangular areas. An average intensity is then calculated by the application 19 for each ROI. A correction factor is then established for each color (i.e., Red and Green) to normalize the sample solution holder 38 to the control solution holder 40. The correction factor (Rfactor or Gfactor) is obtained by calculating a ratio of average intensity of $Red_{Sample}/Red_{Control}$ and a ratio of average intensity of $Greens_{Sample}/Green_{Control}$. The correction factor (Rfactor or Gfactor) may then then be stored within the application 19 for use in later tests.

Next, as seen in operation 1100, a user loads the sample solution holder 38 with the pre-prepared solution containing Au NPs, aptamer, buffer, and saline with the water sample to be tested. Likewise, the user also loads the control solution holder 40 with the pre-prepared control solution. As explained herein, these solutions (absent the sample) may be prepared in advance as part of a kit or reagents usable with a kit so that the user does not have to prepare solutions in the field. The sample solution holder 38 and the control solution holder 40 may be capped off using a top or cap to prevent liquid from leaking out. The sample solution holder 38 and the control solution holder 40 can then be loaded into the openings 43a, 43b of the housing 26 and the cover 41 is closed. Prior to measuring the samples using the system 10 described herein, the samples are allowed to incubate for several minutes (e.g., between 10-15 minutes). Incubation may take place within the reader 20 or outside of the reader 20.

After sufficient time has passed and the sample solution holder 38 and the control solution holder 40 are loaded into the reader 20, a user then turns on the first and second light sources 28, 30 using the switch 34. An image of the transmitted light regions through the sample solution holder 38 and the control solution holder 40 is then captured by the camera 14. This process is seen in operation 1200 of FIG. 3. During this time, the application 19 is running to acquire the image that is generated that will then be analyzed as described herein.

The image contains four (4) different regions with each region being rectangular in shape as defined by the masks 44, 48. Two of the regions are generated by one of the light sources 28 (e.g., red) and correspond to transmissions through the sample solution holder 38 and control solution holder 40, respectively. The remaining two regions are generated by the other of the light sources 30 (e.g., green) and correspond to transmissions through the sample solution holder 38 and control solution holder 40, respectively. Collectively, this includes four regions of illumination ($Red_{Sample}$, $Red_{Control}$, $Green_{Sample}$, $Green_{Control}$).

Next, as seen in operation 1300, an average intensity level is calculated by the application 19 for each region. This is accomplished by defining a region of interest (ROI) about a centroid within the four regions of illumination $Red_{Sample}$, $Red_{Control}$, $Green_{Sample}$, $Green_{Control}$. The region of interest may be a smaller rectangle (e.g., 400×300 pixels) that excludes the edges of each image region. FIG. 2C illustrates ROIs for each of four regions. The average intensity level is then measured by the application for each ROI to generate four respective values: RC, RS, GC, and GS. Next, as seen in operation 1400, the correction factors obtained previously (Rfactor, Gfactor) are multiplied by the respective RS and GS values to produce corrected values. Next, as seen in operation 1500, a ratio of the control intensities is calculated by dividing RC by GC to produce a green:red control ratio (G/R_C). Likewise a ratio of the corrected sample intensities is calculated by dividing RS*Rfactor by GS*Gfactor to produce a green:red sample ratio (G/R_S). In operation 1600, a normalized G/R ratio is then obtained by dividing the G/R_S by the G/R_C. The normalized G/R ratio which is calculated by the software 19 is then used with a stored calibration function or graph within the software 19 to generate a mercury(II) concentration value. This is seen in operation 1700 of FIG. 3. The stored calibration function may be a curve-fitting function, graph, or it may be look-up table of values that is used to generate the mercury(II) concentration value. The stored calibration function may be a default calibration function that is provided by the manufacturer or it may be user generated by, for example, testing with a number of samples having a known concentration of mercury. The calibration function can be stored and be reused.

Note that after initially capturing the colorimetric transmission image of the sample (i.e. obtaining $Red_{Sample}$, $Red_{Control}$, $Green_{Sample}$, $Green_{Control}$), the user can first preview the image on the display 16 before proceeding to digitally analyze/process it. The application 19 can also use an image file already stored on the memory of the mobile phone 12 for processing/testing. With reference to FIG. 4C, after pressing on the "Process" button, the intensity ratios described above between the sample and control regions will be automatically computed on the mobile phone 12. As seen in FIG. 4D, the mercury concentration level (in ppb) of the sample that is calculated by the application 19 is then displayed on the display 16 of the mobile phone 16. The total time taken for calculating the mercury concentration on an Android phone (Samsung Galaxy S II) is <7 seconds. The final test results can be saved on the memory of the mobile phone 12 with a stamp of time and GPS coordinates of the test. The results can also be transmitted or shared with a remote server. For example, multiple different users testing at different locations can upload their obtained results to a secure remote server for spatio-temporal mapping using for example a Google Maps-based interface. This is illustrated in FIG. 4E. In this regard, peer-to-peer sharing of mercury measurements obtained over geographic area of interest can be performed to provide a detailed look at spatio-temporal results. The remote server may store various data fields such as test source type (e.g., tap water, lake, ocean, river stream, pond, etc.), measured mercury concentration, GPS coordinates of location where test was performed, date of test, time of test, make/model of mobile communication device, and user ID. With the same application 19, the results can also be reviewed as a function of time per location using a graph-based interface as seen in FIG. 4F. Note the application 19 described herein may be used on multiple platforms (e.g., Android, IPhone, and the like).

Experimental

Experiments were conducted using the system illustrated in FIGS. 1A and 1B. The reader was used with an Android phone (Samsung Galaxy S II) that included therein a software application that was used to calculate the concentration of mercury in water samples.

Methods

Hardware Design. The optical imaging system was designed for an Android phone (Samsung Galaxy S II) in Autodesk (Inventor) and printed using a 3D printer (Elite, Dimension). All of these electrical and optical elements were consolidated in an opaque cuboid housing and coupled to a base plate with a total weight of ~37 grams. Two LEDs (120 degree illumination angle, SuperBrightLEDs), one green (523 nm, RL5-G16120) and one red (625 nm, RL5-G12120), illuminated the test/sample and control cuvettes simultaneously and were powered by two button cells (3V, CR1620, Energizer). An optical diffuser (made using 3 sheets of A4 printer paper) was inserted between the LEDs and the cuvettes for uniform illumination of each cuvette. The transmitted light through the cuvettes was then collected by a plano-convex lens (focal length f=28 mm, NT65-576, Edmund Optics) and imaged using the smart-phone camera (f=4 mm). This imaging configuration provides an optical demagnification factor of 28/4=7 fold, which permits imaging of both the test and control cuvettes (6.6×6.6 mm in cross section) within the field of view of the phone's CMOS imager chip. To avoid crosstalk of the two-color illumination, a black clapboard was used to separate the light paths of the LEDs before entering the cuvettes, and four (4) rectangular apertures (6.6×5 mm) were added both in front of and behind the cuvettes to spatially filter the transmitted light at each color (i.e., red and green). The acquired images were analyzed in digitally separated red and green channels to further reject possible spectral crosstalk between red and green illumination wavelengths.

Gold Nanoparticle and Aptamer Based Colorimetric Assay.

50 nm citrate-stabilized Au NPs were purchased from nanoComposix. Aptamer sequence of (SEQ ID NO:1) was obtained from Integrated DNA Technologies, San Diego, Calif. All metal salts such as mercury(II) chloride were obtained from Sigma. Stock Au NP solution in 20 mM tris-HCl buffer (TH, pH 8.0) was prepared by centrifugation of raw Au NP-citrate solution, aspiration of the supernatant, and re-dispersion in TH buffer with 20× dilution to give a working concentration of 0.64 nM. Water samples collected from rivers, lakes, and beaches were filtered by 0.2 μm polyethersulfone membrane (Whatman) to remove sand and other solid particles within the test samples. Tap water samples and calibration solutions containing mercury(II) ions prepared in deionized water were used directly without further purification. In a typical measurement procedure, 4 μL of the sample of interest was mixed with 4 μL of 3 μM aptamer (20 mM TH buffer, pH 8.0), followed by a 5 minute reaction period. Next, 400 μL of Au NPs (0.64 nM) in 20 mM TH buffer solution was added and allowed to react for 5 minutes. Finally, 8 μL of 10 mM NaCl was added and incubated for another 10 minutes before being analyzed by the smart-phone device.

UV-vis Spectroscopic Investigation of Water Samples using a Portable Spectrometer.

In comparison measurements made against the Smartphone, a white LED (RL5-W15120, SuperBrightLEDs) was used as the light source, and the transmission signal that passed through a standard 1-cm cuvette was collected by a 600-μm diameter optical fiber and measured by a portable spectrometer (HR2000+, Ocean Optics). The background spectrum was recorded using deionized water as a blank control sample. Each spectrum was collected with an exposure time of 1 ms and scanned 500 times for averaging in order to improve the signal-to-noise ratio of each UV-vis spectroscopic measurement.

Plasmonic Colorimetric Assay and Measurement of Mercury(II) Ion Concentration.

The characteristic color change of Au NPs from red to purple or blue upon aggregation that is induced by mercury (II) ion binding events constitutes the basis of the Au NP-based colorimetric detection assay. However, most Au NP-based probes require a surface modification step to conjugate mercury(II)-specific ligands onto Au NPs, and the LOD varies based on the capturing ligand that is selected. Here, an alternative approach was used which utilizes the strong affinity of the thymine-rich aptamer (Apt) sequence to mercury(II) ions and citrate-stabilized Au NPs as colorimetric signal transducers to generate a high detection sensitivity. In this protocol, Au NPs are used without the need for surface functionalization steps, which greatly facilitates field use. In a typical mercury detection experiment, 0.64 nM of Au NPs (50 nm diameter) are mixed with 3 μM aptamer (SEQ ID NO:1) in 20 mM Tris-HCl buffer (pH 8.0) to form the probe solution. Next, 4 μL of water sample solution is added to the probe solution and incubated for 5-10 minutes. Aptamer forms a protective layer on the surface of Au NPs, which prevents them from aggregation even in a high salt environment such as 10 mM NaCl. However, this aptamer layer will be stripped off by the presence of mercury(II) ions due to the formation of more stable T-$Hg^{2+}$-T complexes. As a result, the unprotected Au NPs can undergo distinct color transition from red to blue in the presence of NaCl and this spectral shift is detected to quantify mercury concentration using the dual-wavelength Smartphone based colorimetric reader.

A representative smart-phone captured image of Au NP probe solutions with and without mercury(II) ions is depicted in FIG. 2B. Each cuvette was illuminated by red and green LEDs at different spatial locations and separated by two rectangular apertures that are 3 mm apart from each other as seen in FIG. 2B. Note that the dimensions of FIG. 2B reflect what was used in the experiments and is not necessarily required and dimensions thus may be different than those illustrated. The illumination spots of the LEDs were sufficiently large to cover both the sample and control cuvettes (2 mm apart). This dual-illumination color and dual-cuvette configuration forms four readable signals in a single image frame, namely red control (RC), red sample (RS), green control (GC), and green sample (GS) signals. To quantify the mercury contamination in a given water sample, the acquired transmission image of these cuvettes (sample and control) is first digitally split into red (R) and green (G) channels as seen in FIG. 2C to further minimize the spectral crosstalk between these two colors. The centroids of each rectangular aperture are automatically localized by a detection algorithm and a rectangular region of interest (ROI, 400×300 pixels) around each of these four centroids is then used to calculate the averaged transmission signal for each ROI, yielding RC, RS, GC and GS signals. Note that RC and RS are calculated using the Red channel image whereas GC and GS are calculated using the Green channel image, both of which are digitally separated from the raw RGB image captured by the mobile phone camera sensor. The transmission intensity of the sample cuvette is further normalized to that of the control cuvette by placing two identical deionized water samples in both cuvette positions, leading to an illumination normalization factor of 1.15 for the red LED (Rfactor) and 0.98 for the green LED (Gfactor). The calibration ratio of the control cuvette (G/R_C) was obtained by taking the ratio of the GC and RC. Similarly, the calibration ratio of the sample cuvette (G/R_S) was obtained by taking the ratio of GS×Gfactor and RS×Rfactor. Finally, the ultimate normalized green-to-red signal (i.e., normalized G/R) for a given water sample was computed by taking the ratio of G/R_S and G/R_C. These calculations are automatically implemented using a custom-designed Android application running on the same Smartphone.

Android based Smart Application for Mercury Quantification.

A custom-designed Android application was developed that allows for mobile testing and sharing of mercury quantification results. After attaching the colorimetric mercury measurement device onto the Smartphone camera unit as seen in FIGS. 1A and 1B, the user can hold the mobile phone horizontally and then run mercury tests using this smart application. From the main menu of the application, the user can start a new test, create a device-specific calibration curve, view previously run tests, share the test results and review the operating instructions (FIG. 4A). The user can calibrate the application for attachment-specific variations by imaging e.g., mercury contaminated control samples at known concentrations (FIG. 4B). These calibration curves can be stored and reused by various different devices/attachments. After capturing a colorimetric transmission image of the sample, the user can first preview the image on the screen before proceeding to digitally analyze/process it (FIG. 4C). The application can also use an image file already stored on the phone memory for processing/testing. After pressing on the "Process" button, the transmission signal ratios between the sample and control regions will be automatically computed on the phone, following the image processing steps discussed in the previous section. A previously stored calibration curve is used to convert the calculated signal ratio into the mercury concentration level of the sample (in ppb) and the results are then displayed on the screen of the phone (FIG. 4D). The total time taken for calculating the mercury concentration on the Android phone (Samsung Galaxy S II) is <7 seconds. The final test results can be saved on the phone memory with a stamp of time and GPS coordinates of the test and can also be shared with a secure server for spatio-temporal mapping using for example a Google Maps-based interface (FIG. 4E). With the same Android application, the results can also be reviewed as a function of time per location using a graph-based interface (FIG. 4F).

Calibration and Specificity Tests.

Figure 5:
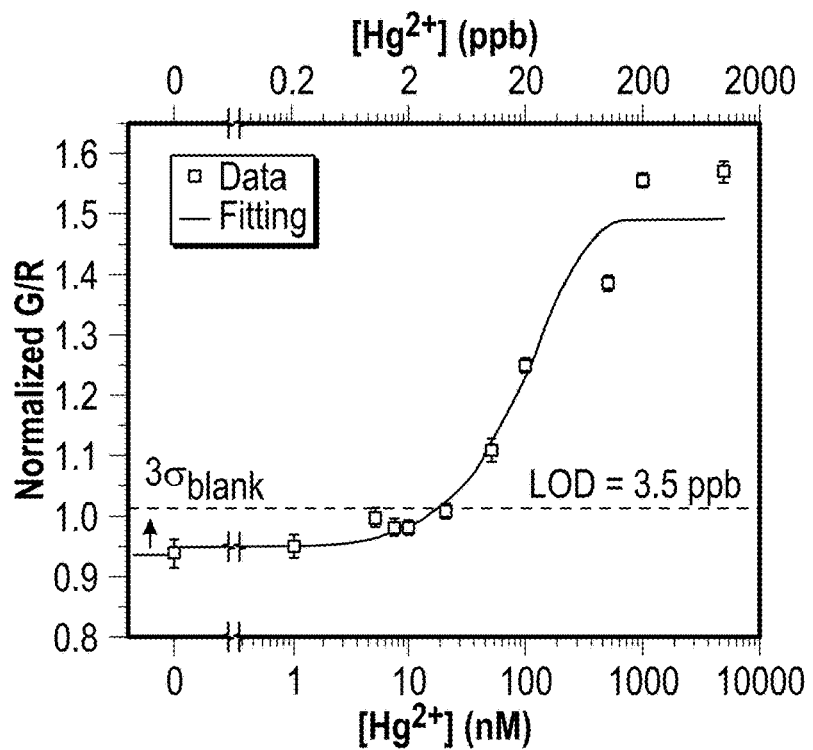
FIG. 5 illustrates a dose-response curve of the gold nanoparticles and aptamer-based plasmonic colormetric assay that is run on a Smartphone mobile communication device. Each measurement at a given concentration was repeated three times. The curve was fitted by an exponential function with a coefficient of determination ($R^2$) of 0.96. An LOD of 3.5 ppb for $Hg^{2+}$ was obtained based on the G/R ratios of a control sample ($[Hg^{2+}]=0$) plus three times the standard deviation of the control (dashed line).
Figure 9A:
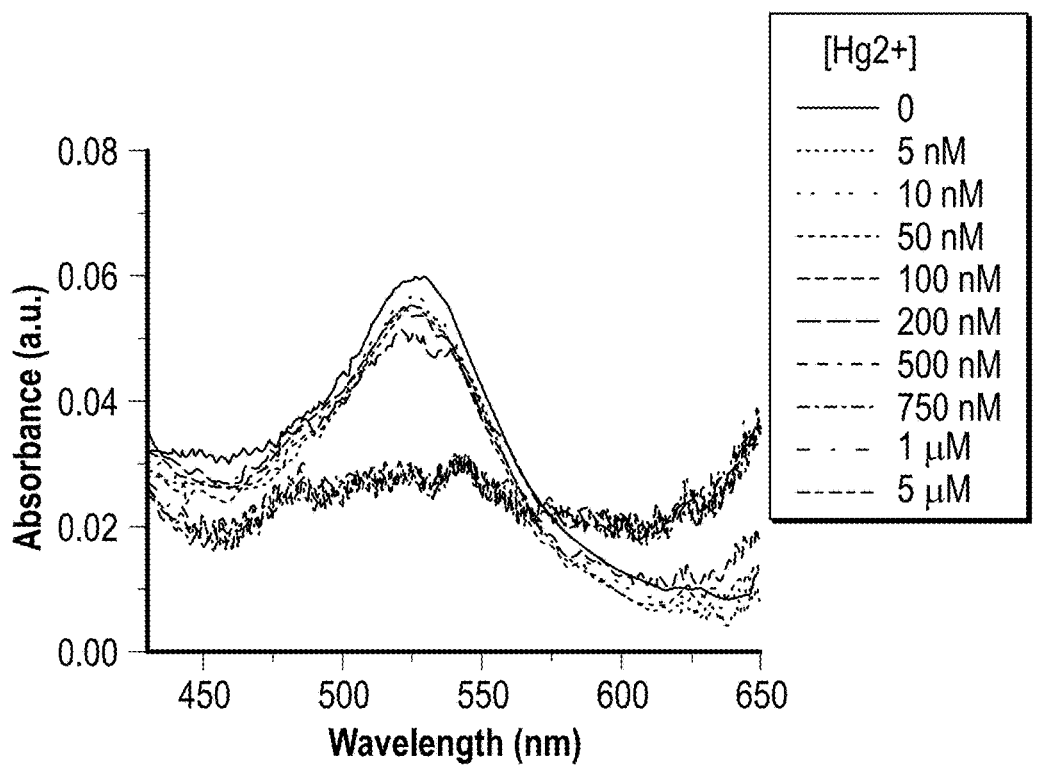
FIG. 9A illustrates UV-vis spectra of Au NP probe solutions ([Au NP]=0.64 nM, Apt=30 nM) treated with different concentrations of $Hg^{2+}$ (ranging from 0 to 5 μM)
Figure 10:
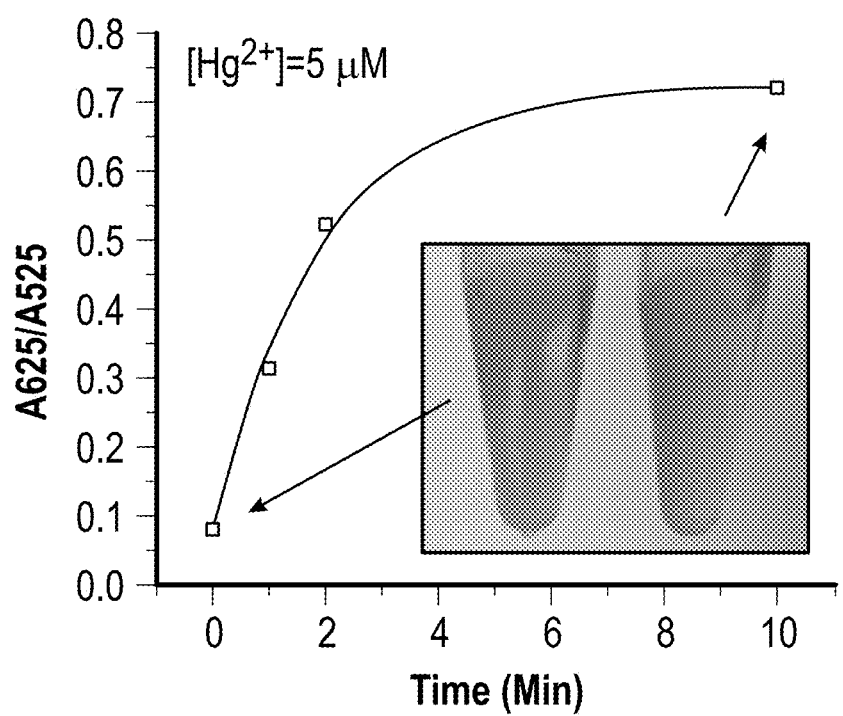
FIG. 10 illustrates a graph of the time-dependent UV-vis spectroscopic measurements showing the dynamics of the gold nanoparticle and aptamer based assay ([Au NP]=0.64 nM, [Apt]=30 nM, [$Hg^{2+}$]=5 μM). Inset shows a photograph of the Au NP probe solution before and after 10 min of reaction with mercury(II) ions.

In the Smartphone-based mercury detection platform, each normalized G/R ratio computed from a captured RGB image corresponds to a specific mercury concentration value (ppb). The Android application includes a default calibration curve, which was obtained by measuring the normalized G/R ratios of a set of known concentration mercury(II) solutions ranging from 0 to 5 µM (see FIG. 5). The values of these normalized G/R ratios increased as the concentration of mercury(II) ions rose above 10 nM, and reached saturation at >1000 nM (FIG. 4). The signal increase in the 10-1000 nM range is mainly due to the aggregation of Au NPs which is triggered by the mercury(II) ion concentration. This Au NP aggregation process relatively enhances the extinction at the red wavelength (e.g., 625 nm) while it reduces the extinction at the green wavelength (e.g., 523 nm), which is also confirmed by UV-vis spectroscopic measurements as seen in FIG. 9A. This plasmon-resonance based wavelength shift occurred rapidly after around 5 minutes as seen in FIG. 10 demonstrating a quick response time for the NP/aptamer based colorimetric assay making it appropriate for use in field settings. As a result of these plasmonic changes due to NP aggregation, the transmission signal of the red channel relatively decreased, whereas the transmission of the green channel increased. Therefore, the final G/R ratio of a sample increased as the mercury(II) ion concentration is increased, which is also illustrated in the calibration curve presented in FIG. 5.

Figure 9B:
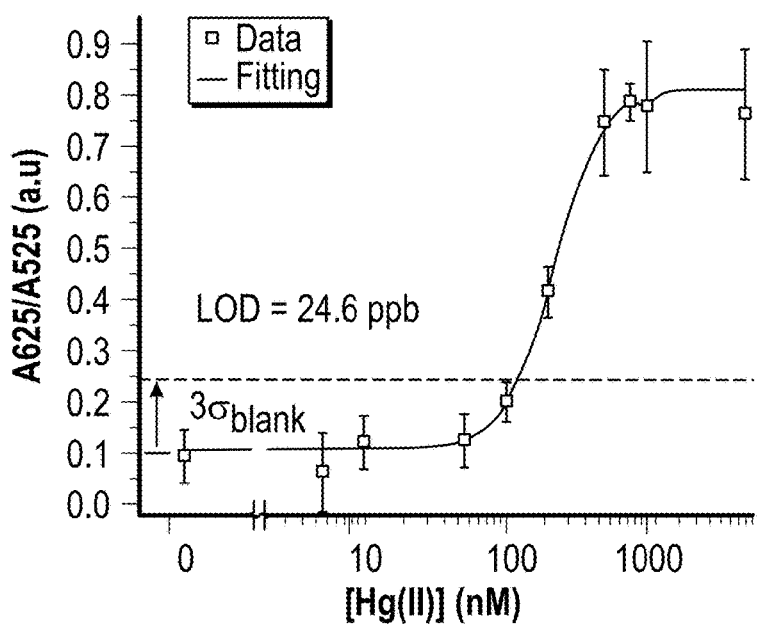
FIG. 9B illustrates the calibration curve of the UV-vis spectrometer based measurements by plotting the extinction ratio of 625 and 525 nm against the concentration of mercury(II) ions.

To determine the LOD of the Smartphone based colorimetric assay, the normalized G/R values of a control sample were measured (i.e., [$Hg^{2+}$]=0, [Au NPs]=0.64 nM, [Apt]=30 nM) which resulted in a signal level of 0.940±0.025 ($\mu_{blank} \pm \sigma_{blank}$). The LOD was then determined by the mean of this control sample plus three times its standard deviation ($\mu_{blank}+3\sigma_{blank}$, see the dashed line in FIG. 5) which corresponds to a mercury(II) ion concentration of approximately 17.3 nM or ~3.5 ppb. Quite interestingly, the LOD of the Smartphone based dual-color ratiometric platform was more than six (6) times better than the LOD of the exact same assay measured by a portable UV-vis spectrometer (Ocean Optics, HR2000+, Ocean Optics, Fla.), which resulted in 123 nM or 24.6 ppb LOD as seen in FIG. 9B. More importantly, the LOD of mercury(II) ions using the Smartphone based field-portable device has the same order of magnitude as EPA's mercury(II) reference concentration for drinking water (i.e., 2 ppb) and also satisfies the WHO guideline value for mercury(II) concentration (i.e., 6 ppb).

Figure 6:
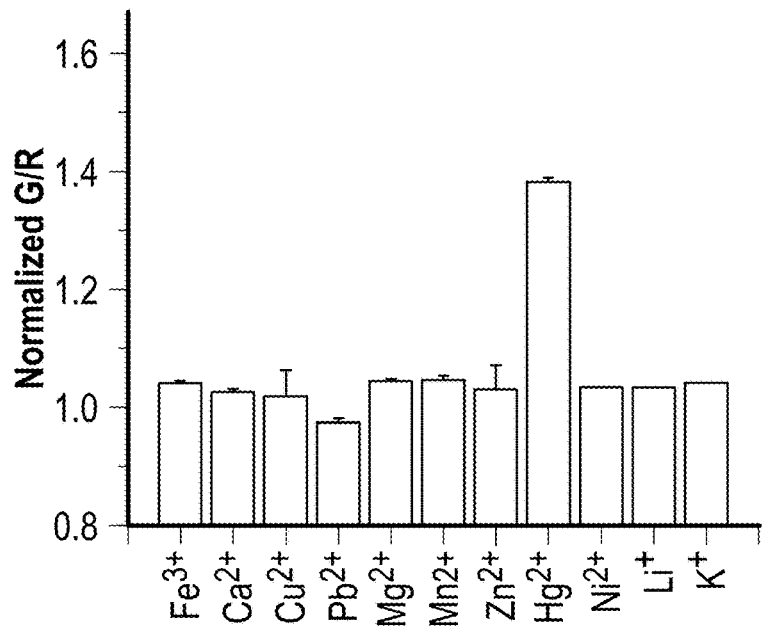
FIG. 6 illustrates the specificity of tests of the gold nanoparticles and aptamer-based plasmonic mercury assay for different metal ions (500 nM). Each measurement was repeated three times.
Figure 9C:
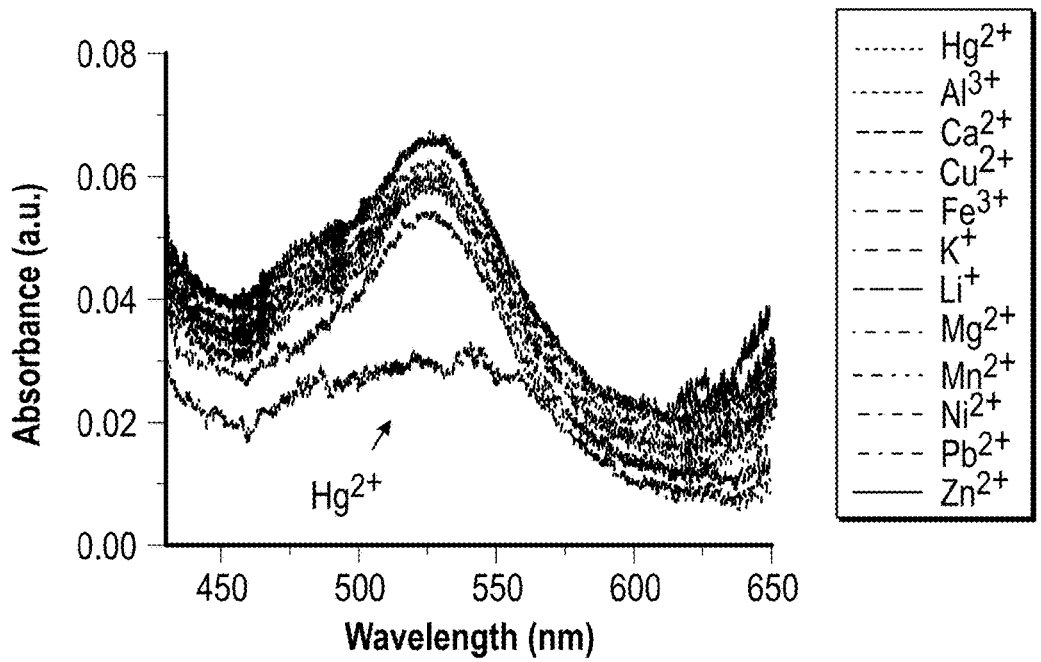
FIG. 9C illustrates UV-vis spectra of Au NP probe solutions in exposure to different metal ions. All the metal ion samples had the same concentration at 500 nM.
Figure 9D:
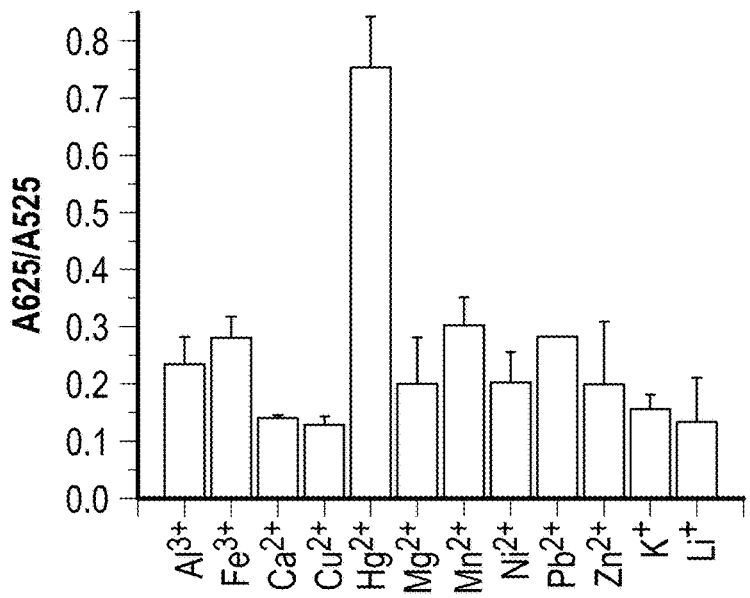
FIG. 9D illustrates a plot of the extinction ratios showing a good specificity of the Au NP based assay toward detection of mercury(II) ions only.

Next, specificity tests were performed by challenging the same colorimetric plasmonic nanoparticle and aptamer assay with different metal ions, such as $Fe^{3+}$, $Ca^{2+}$, $Cu^{2+}$, $Pb^{2+}$, etc. as illustrated in FIG. 6. The concentrations of all these metal ion samples were prepared to be 500 nM, and the experiments revealed that, except mercury(II) ions, the other metal ion samples yielded a signal level that is comparable to control samples, verifying the specificity of the assay toward detection of $Hg^{2+}$. The same specificity performance was also confirmed independently by UV-vis spectroscopic measurements as illustrated in FIG. 9C and FIG. 9D.

Mapping of Mercury Concentration in Water Samples in California.

Figure 7:
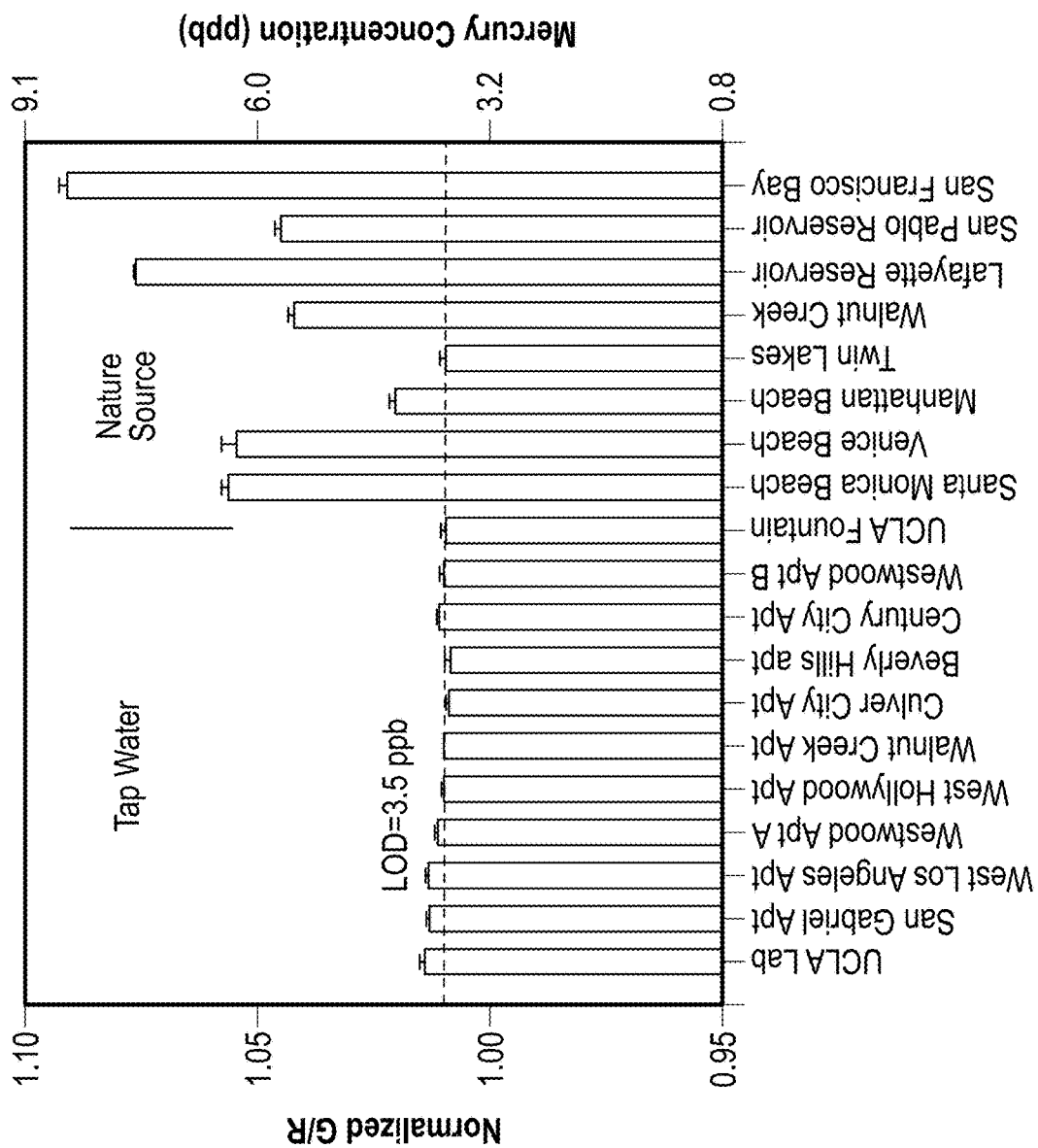
FIG. 7 illustrates the Smartphone-based mercury detection results for eleven (11) tap water samples and eight (8) natural samples collected in California, USA. Each measurement was repeated three times. Note that the measurements are plotted against the G/R ratios, which makes the presented scale of the mercury concentration (ppb) nonlinear, between 0.8 and 9.1 ppb.

The performance of the Smartphone enabled testing device was tested with water samples including city tap water and natural water samples collected at over fifty (50) different locations in California. FIG. 7 summarizes the measurement results for nineteen (19) of these samples collected from various apartments (tap water), rivers, lakes, and beaches in California coast. The results suggest that all the city tap water samples have undetectable levels of mercury(II) ions since the signal readings are at the same level as the LOD. However, the measurements for the water samples collected from natural sources reveal higher mercury concentration levels, ranging from 3.7 to 8.6 ppb as illustrated in FIG. 7. The samples that are found to contain mercury(II) ion concentrations above 6 ppb, i.e., the safety level recommended by WHO, are mostly from ocean samples, with the worst being from the San Francisco Bay. The observation that the mercury content in ocean water samples is higher compared to fresh water is probably because the ocean is at the end of mercury's global transport pathway in the environment and thus might exhibit higher pollution levels.

Figure 8A:
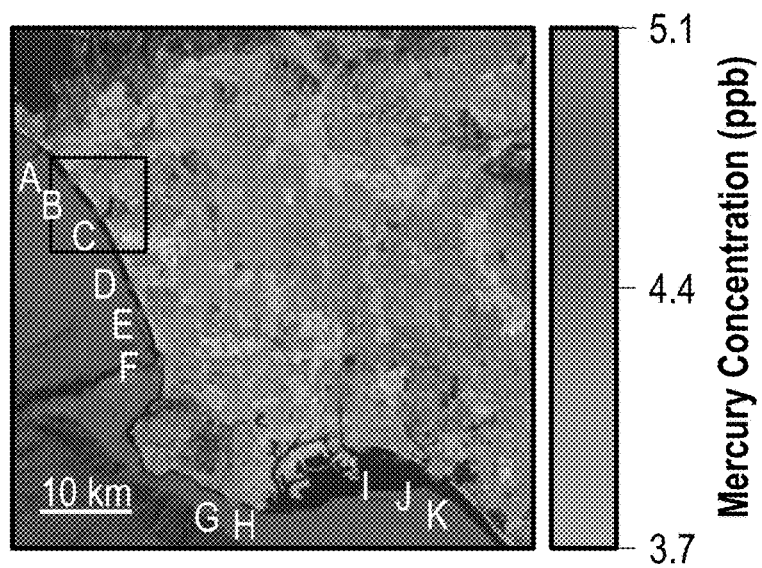
FIG. 8A illustrates a spatio-temporal mapping of mercury contamination in Los Angeles coastal area.
Figure 8B:
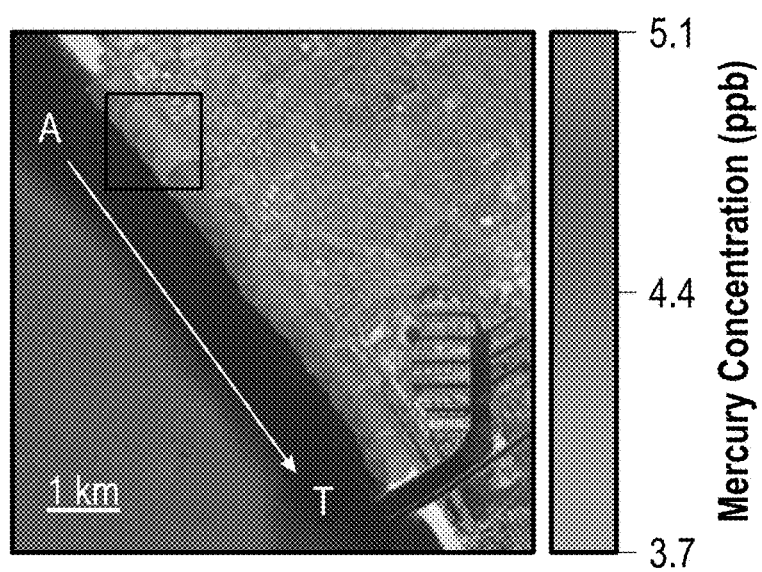
FIG. 8B illustrates the enlarged region of the square ROI in FIG. 8A
Figure 8C:
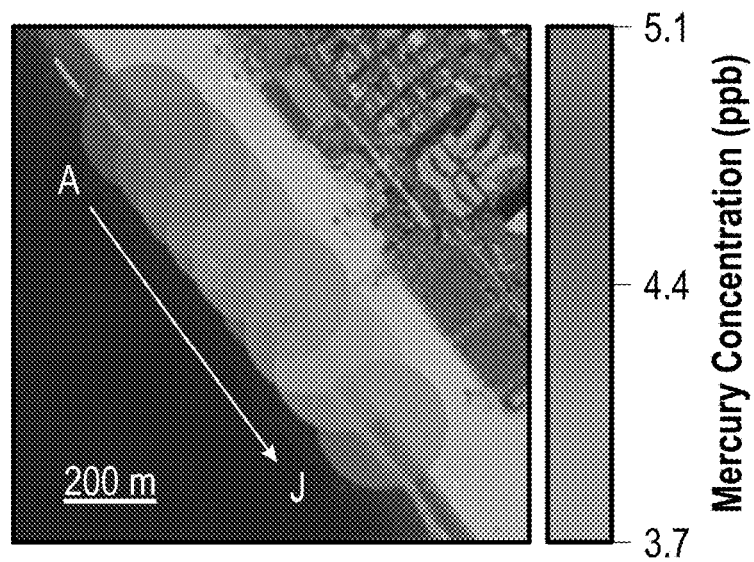
FIG. 8C illustrates the enlarged region of the square ROI in FIG. 8B.
Figure 8D:
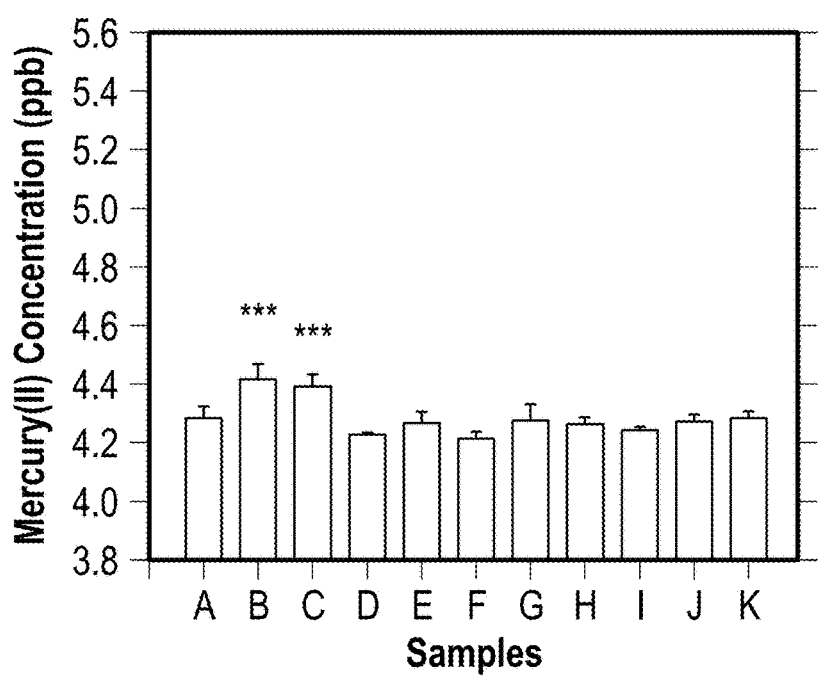
FIGS. 8D-8F illustrate corresponding mercury concentration readings in FIGS. 8A-8C, respectively. All the data points were measured three times. P values were calculated via two-sample Students' T test by setting target data set as one population and the rest of the data sets as the other.  represents p<0.01, and * represents p<0.001.
Figure 8E:
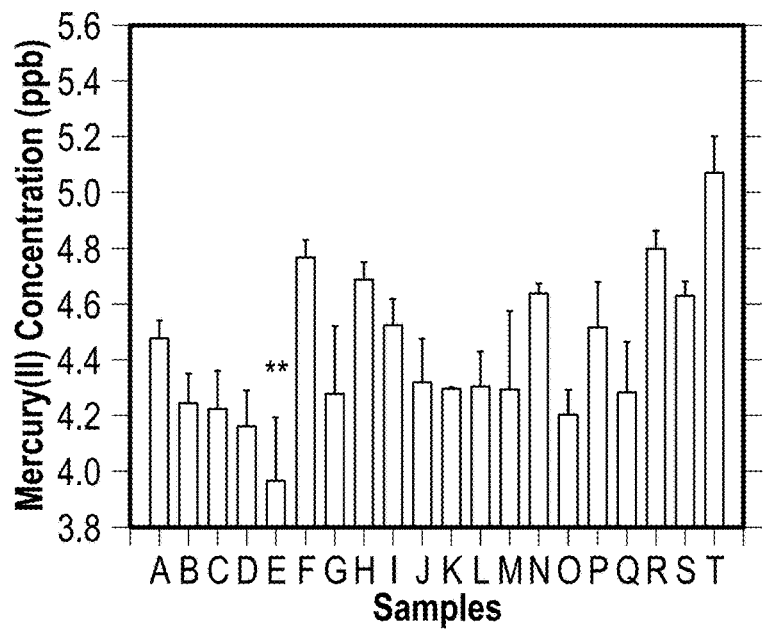
Figure 8F:
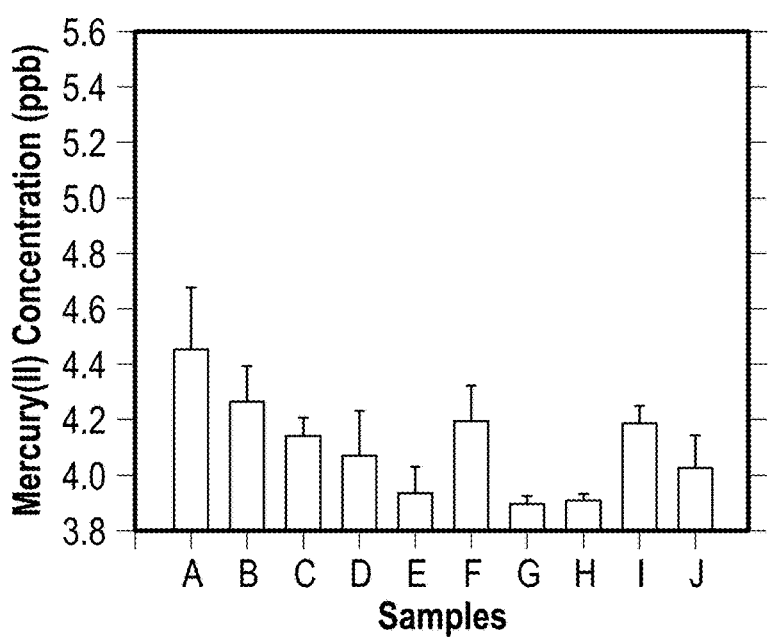

As one of its major advantages, the handheld Smartphone based mercury detection platform is also able to generate spatio-temporal contamination maps for e.g., environmental monitoring. To do so, GPS coordinates (and time of test) were recorded for each water sample that was tested and all the other sample related information such as measurement results and dates were sent to a secure server using the Smartphone application for mapping of the results. FIGS. 8A-8C represent three Smartphone generated mercury monitoring maps, where the spatial resolution of the maps is determined by the sampling density. For instance, in FIG. 8A, samples were collected and measured at a low density of ~0.2 measurements/km; in FIG. 8B and FIG. 8C, higher resolution was shown by increasing the sampling density to 3.3 and 20 measurements/km, respectively. FIGS. 8D, 8E, and 8F show histogram plots corresponding to the mercury (II) concentrations that are displayed in FIGS. 8A, 8B, and 8C, respectively, with a better visualization of the variation of mercury(II) levels within a given area. Interestingly, some locations such as points B and C in FIG. 8A and FIG. 8D had statistically higher mercury(II) levels than the rest with very small p values (<0.001) determined by standard Students' t test. Further investigation of this area indicated that the square ROI in FIG. 8A included a marina hosting yachts and boats FIG. 8B, which possibly form the major source of heavy metal pollution in that particular region. Mercury(II) ion concentration near the marina also formed a weak gradient (from A to T) as illustrated in FIG. 8B and FIG. 8E, with the closest point to the marina having the highest mercury(II) concentration (i.e., the point T in FIG. 8B and FIG. 8E). Point E in FIG. 8E was statistically lower in mercury(II) concentration (p<0.01) compared to other locations within the same region of interest, and this observation was confirmed by higher resolution mercury(II) mapping in FIGS. 8C and 8F. In addition to spatial mapping of contamination, the option of monitoring the level of mercury concentration as a function of time for a specific location is also feasible using the Smartphone based sensing platform as illustrated in FIG. 4F.

As disclosed herein, a sensitive and cost-effective Smartphone-based mercury(II) ion sensor platform has been described which utilizes a battery-powered opto-mechanical reader attached to the existing camera module of a Smartphone to digitally quantify mercury concentration using a plasmonic Au NP and aptamer based colorimetric assay. A two-color ratiometric detection method was employed using LEDs at 523 and 625 nm, and a custom-developed Android application for rapid digital image processing of the captured transmission images on the same phone. The LOD of mercury(II) ions with this mobile device is found to be 3.5 ppb, which is on the same order of magnitude with the maximum allowable level of mercury(II) ions in drinkable water defined by the U.S. EPA (2 ppb) and WHO (6 ppb). Moreover, a geospatial mercury(II) contamination was generated map by measuring more than 50 samples collected in California from various sources including tap, river, lake, and ocean water samples. The cost-effective design, portability and data connectivity of this sensitive heavy metal detection device integrated onto a mobile phone could be rather useful for distributed sensing, tracking and sharing of water contamination information as a function of both space and time, globally.

While embodiments of the present invention have been shown and described, various modifications may be made without departing from the scope of the present invention. For example, different colored light sources could be used. In addition, there could be more than two light sources to add greater sensitivity. The invention, therefore, should not be limited, except to the following claims, and their equivalents.

What is claimed is:

1. A system for analyzing a water sample for mercury with a mobile electronic device having a camera comprising:
   a reader configured for securement to the mobile electronic device over the camera, the reader further comprising:
      a sample solution holder and a control solution holder;
      a power source operatively coupled to a first light source and a second light source configured to illuminate the sample solution holder and the control solution holder with a First Color and a Second Color;
      a mask interposed between the first and second light sources and the sample solution and control solution holders, the mask comprising a first set of apertures disposed over the sample solution holder and the control solution holder and configured to be illuminated by the first light source and a second set of apertures disposed over the sample solution holder and the control solution holder and configured to be illuminated by the second light source;
      a lens disposed in the reader and positioned adjacent to the camera;
      a solution containing sodium chloride, nanoparticles, and thymine-rich aptamer contained in both the sample solution holder and the control solution holder, the sample solution holder also containing the water sample therein; and
   wherein the mobile electronic device is configured to capture an image of transmitted light passing through the control solution holder and the sample solution holder from the first and second light sources, wherein the image contains four separate regions of interest (First Color$_{Sample}$, First Color$_{Control}$, Second Color$_{Sample}$, and Second Color$_{Control}$) and wherein the mobile electronic device outputs a concentration of mercury within the water sample based on a normalized color ratio obtained from a measured average intensity level obtained at each of the four separate regions of interest (First Color$_{Sample}$, First Color$_{Control}$, Second Color$_{Sample}$, and Second Color$_{Control}$), wherein the normalized color ratio comprises a ratio of First Color$_{Sample}$/Second Color$_{Sample}$ and First Color$_{Control}$/Second Color$_{Control}$.

2. The system of claim 1, further comprising a diffuser interposed between the first and second light sources and the mask.

3. The system of claim 1, further comprising a second mask interposed between the sample and control solution holders and the lens.

SEQUENCE LISTING

<160> NUMBER OF SEQ ID NOS: 1

<210> SEQ ID NO 1
<211> LENGTH: 10
<212> TYPE: DNA
<213> ORGANISM: Artificial Sequence
<220> FEATURE:
<223> OTHER INFORMATION: Oligonucleotide

<400> SEQUENCE: 1
tttttttttt    10

4. The system of claim 1, first light source comprises a green LED and the second light source comprises a red LED.

5. The system of claim 4, wherein the normalized color ratio comprises a ratio of G/R_S and G/R_C, wherein G/R_S comprises a green:red sample ratio and wherein G/R_C comprises a green:red control ratio.

6. The system of claim 1, wherein the nanoparticles comprise gold nanoparticles.

7. The system of claim 1, wherein the thymine-rich apatamer comprises SEQ ID NO:1.

8. The system of claim 1, further comprising an opaque divider interposed between the first and second light source.

9. The system of claim 1, wherein the mobile electronic device contains a calibration curve or function therein and wherein the mobile electronic device outputs a concentration of mercury based at least in part on the calibration curve.

10. The system of claim 1, wherein the mobile electronic device outputs a time stamp and GPS coordinates associated with each sample reading.

11. The system of claim 1, further comprising at least one remote computer configured to store sample results from the mobile electronic device.

12. The system of claim 1, wherein the mobile electronic device comprises a software application executable on the mobile electronic device, the software application executed by at least one processor of the mobile electronic device to output the mercury concentration of the water sample.

13. The system of claim 1, wherein a limit of detection of the system is about 3.5 ppb.

14. The system of claim 1, wherein the reader comprises a base plate configured to be removable secured to a face of the mobile electronic device.

15. A method of measuring a concentration of mercury in a water sample comprising:
   securing a reader to a mobile electronic device having a camera therein, the reader comprising a sample solution holder and a control solution holder; a power source operatively coupled to first and second light sources configured to illuminate a sample solution holder and a control solution holder at two different colors; and a lens disposed in the reader and adjacent to the camera;
   loading the sample solution holder with the water sample, gold nanoparticles, thymine-rich aptamers, and sodium chloride;
   loading the control solution holder with the gold nanoparticles, thymine-rich aptamers, and, and sodium chloride;
   illuminating the sample solution holder and the control solution holder with first and second light sources emitting light;
   capturing an image of light passing through the sample solution holder and the control solution holder, wherein the image comprises two control regions of interest and two sample regions of interest;
   the mobile electronic device calculating an average intensity for each of the two control regions of interest and each of the two sample regions of interest and generating intensity ratios for the sample regions of interest and control regions of interest, respectively, at each color using the respective average intensities obtained for the two control regions of interest and the two sample control regions of interest; and
   the mobile electronic device calculating a normalized color ratio based on the generated intensity ratios for the sample regions of interest and control regions of interest at each color and outputting a concentration of mercury based on the normalized color ratio.

16. The method of claim 15, wherein the first light source comprises a green light source and the second light source comprises a red light source.

17. The method of claim 15, further comprising the mobile electronic device mapping a location of the water sample onto a mapping application run on the mobile electronic device.

18. The method of claim 15, further comprising the mobile electronic device transmitting the concentration of mercury to a remote computer.

19. The method of claim 15, wherein the concentration of mercury is obtained from a calibration graph or function stored within the mobile electronic device.

* * * * *